(12) United States Patent
Salvati et al.

(10) Patent No.: US 7,087,636 B2
(45) Date of Patent: Aug. 8, 2006

(54) FUSED HETEROCYCLIC COMPOUNDS AND ANALOGS THEREOF, MODULATORS OF NUCLEAR HORMONE RECEPTOR FUNCTION

(75) Inventors: Mark E. Salvati, Lawrenceville, NJ (US); James Aaron Balog, Lambertville, NJ (US); Dacia A. Pickering, Lawrenceville, NJ (US); Hong Zhu, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 219 days.

(21) Appl. No.: 10/322,276

(22) Filed: Dec. 18, 2002

(65) Prior Publication Data

US 2003/0181728 A1 Sep. 25, 2003

Related U.S. Application Data

(60) Provisional application No. 60/341,962, filed on Dec. 19, 2001.

(51) Int. Cl.
*A61K 31/40* (2006.01)
*C07D 487/02* (2006.01)

(52) U.S. Cl. ....................... 514/412; 548/453
(58) Field of Classification Search ............... 548/453
See application file for complete search history.

(56) References Cited

U.S. PATENT DOCUMENTS

| 3,261,845 | A | 7/1966 | Bockstahler |
| 4,476,184 | A | 10/1984 | Lubowitz et al. |
| 4,533,737 | A | 8/1985 | Ryang |
| 4,562,255 | A | 12/1985 | Freed et al. |
| 4,582,886 | A | 4/1986 | Ryang |
| 5,399,725 | A | 3/1995 | Poss et al. |
| 5,530,089 | A | 6/1996 | Sheppard et al. |
| 5,929,146 | A | 7/1999 | Amos et al. |

FOREIGN PATENT DOCUMENTS

| EP | 0 626 384 A1 | 11/1994 |
| EP | 0 678 507 A1 | 10/1995 |
| WO | WO 01/19831 | 3/2001 |
| WO | WO 02/00617 | 1/2002 |
| WO | WO 02/24702 | 3/2002 |

OTHER PUBLICATIONS

Chemical Papers (1995), 49 (4), 186–91 CAS Abstract Only.*
Chemical Abstracts, vol. 57, p. 16561f (1962).
Chemical Abstracts, vol. 65, p. 15325h (1966).
Chen et al., Gaodeng Xuexiao Huaxue Xuebao, vol. 4, No. 2, pp. 201–206 (1983).
Dominianni, S.J. et al., "Some Derivatives of 7–Oxabicyclo [2.2.1]heptane–exo–cis–2,3–dicarboxylic Acid", J. Med. Chem., vol. 14, p. 175 (1971).
Fang, Y. et al., "Synthesis of the Epoxidised/Bromizated Derivatives of Norcantharidin", Huaxue Tongbao, No. 1, pp. 27–30 (1994).
Fišera, L'. et al., "Stereoselectivity of the Diels–Alder Cycloadditions, Sodium Borohydride Reduction and 1,3–Dipolar Cycloadditions to Furan Derivatives", Chem. Papers, vol. 49, No. 4, pp. 186–191 (1995).
Gribble, G.W. et al., "Syntheses and Diels–Alder Cycloaddition Reactions of 4H–Furo[3,4–b]indoles. A Regiospecific Diels–Alder Synthesis of Ellipticine", J. Org. Chem., vol. 57, pp. 5878–5891 (1992).
Grogan, C.H. et al., "Bicyclic Imides and Isoindolines", J. Med. Chem., vol. 6, p. 802–805 (1963).
Jolivet, P.J., "A L'Étude de L'Anhydride Endoxo–3,6 $\Delta_4$ Tétrahydrophtalique", Ann. Chim., vol. 5, pp. 1165–1217 (1960).
Joshi, B.S. et al., "Synthesis & Anticonvulsant Activity of 7–Oxabicyclo[2.2.1]heptane Derivaties: Part I—N–Alkyl, N–Aryl & N–Heteroaryl Derivatives of 3,6–Epoxyhexahydrophthalimide", Indian Journal of Chemistry, vol. 22B, pp. 131–135 (1983).
Kobayashi, T. et al., "A Novel Skeletal Rearrangement of 2–Azabicyclo[2.2.1]hept–5–ene–3–carboxylic Acid Derivatives into 2–Oxabicyclo[3.3.0]–oct–7–en–3–ones under Acidic Conditions", Bull. Chem. Soc. Jpn., vol. 65, pp. 61–65 (1992).
Kobayashi, T. et al., "Norbornadiene–Fused Heterocycles: Synthesis and Cycloaddition Reactions of 2–Aryl–4,7–dihydro–4,7–methano–2H–isoindoles and 4,7–Dihydro–4,7–methanoisobenzofuran", Bull. Chem. Soc. Jpn., vol. 68, pp. 3269–3275 (1995).
Liu, J. et al., "A Study on Antitumor Chemotherapeutic Agents—Synthesis of Cantharidine Derivatives", Yaoxue Xuebao, vol. 15, No. 5, pp. 271–277 (1980) (with English abstract).
Liu, J.–Y. et al., "Studies on Antitumor Chemotherapeutic Agents II. Synthesis of Cantharidine Derivatives and Analogues", Acta Pharmaceutica Sinica, vol. 18, No. 10, pp. 752–759 (1983) (with English abstract).
Mel'nikow, N.N. et al., "Some Derivatives of 4,5–dichloro–3,6–endoxohexahydrophthalic Acid", Zh. Obshch. Khim., vol. 29, pp. 968–970 (1956) (English translation).

(Continued)

*Primary Examiner*—Kamal Saeed
(74) *Attorney, Agent, or Firm*—Anstasia P. Winslow

(57) ABSTRACT

Fused cyclic compounds, methods of using such compounds in the treatment of nuclear hormone receptor-associated conditions such as cancer and immune disorders, and pharmaceutical compositions containing such compounds.

25 Claims, No Drawings

OTHER PUBLICATIONS

Mikhailyuchenko, N.G. et al., "Polyfural(aryl)alkanes and Their Derivatives. 9. Polyfuryl(aryl)methanes in the Diels–Alder Reaction", Khimiya Geterosiklicheskikh Soedinenii, No. 6, pp. 642–649 (1993) (English translation).

Mueller, R.H. et al., "Diastereoselective Reaction of a Grignard Reagent with Chiral Imides: A Practical Preparation of a Key Intermediate in the Synthesis of Ifetroban Sodium", Organic Process Research & Development, vol. 1, pp. 14–19 (1997).

Padwa, A. et al., "Cyclic Carbonyl Ylide Formation from the Rhodium (II) Acetate Catalyzed Reaction of 1–diazoalkanediones", Tetrahedron Letters, vol. 30, No. 3, pp. 301–304 (1989).

Salakhov, M.S. et al., "Stereochemistry of the Adducts of Some Polychlorocyclopentadienes with the Anhydride and N–phenylimide of 3,6–epoxy–4–cyclohexene–1,2–dicarboxylic Acid", Zhurnal Organicheskoi Khimii, vol. 14, No. 6, pp. 1200–1202 (1978) (English translation).

SciFinder Search Results, Aug. 16, 2000.

SciFinder Search Results, Registry No. 10487–45–3, Aug. 16, 2000.

SciFinder Search Results, Registry No. 99542–17–3, Jun. 20, 2001.

SciFinder Search Results, Registry No. 107919–15–3.

SciFinder Search Results, Registry No. 146797–53–7, Sep. 11, 2000.

Srivastava, A. et al., "Diels–Alder adduct of 2–methyl furan and N–phenyl maleimides: Configurational assignment through conformational analysis about N–C (phenyl) bond", Natl. Acad. Sci. Letters, vol. 15, No. 2, pp. 41–44 (1992).

Tsuchiya, T. et al., "Photochemistry—IX: Formation of Cyclopropenyl Ketones and Furans from Pyridazine N–Oxides by Irradiation", Tetrahedron, vol. 29, No. 18, pp. 2747–2751 (1973).

Xu, B., "Pharmacology of some natural products of China", Trends in Pharmacologial Sciences, vol. 2, No. 10, pp. 271–272 (1981).

Yur'ev, Y.K. et al., V. Synthesis of N–(trichloromethylmercapto)imide Derivatives of 3,6–endoxohexahydrophthalic Acid, J. Gen. Chem., vol. 30, pp. 869–872 (1960) (English translation).

Zhang, S., "A Study on Antitumor Chemotherapeutic Agents—Synthesis of N–Cantharidine Derivatives", Acta Pharmaceutica Sinica, vol. 16, No. 10, pp. 784–786 (1981) (with English abstract).

Alekperov, N.A. et al., "Effect of the Nature of the Groups at the Bridging Carbon Atom on the Formation of Endo, Endo– and Endo–Exo–Anhydrides and Imides of the 3,6–epoxytricyclo[6.2.1.0$^{2,7}$]–undecene Series", Zhumal Organischeskoi Khimii, vol. 16, No. 4, pp. 770–777 (1980) (English translation).

Benitez, A. et al., "Site Selectivity of the Diels–Alder Reactions of 3–[1–(*tert*–Butyldimethylsilyloxy)vin–1–yl] furan and 3–(Propen–2–yl)furan. Synthesis of 4–Substituted Benzofurans", J. Org. Chem. vol. 61, pp. 1487–1492 (1996).

Bockstahler, E.R. et al., "7–Oxabicyclo[2.2.1]heptane–2, 3–dicarboximides with Anticonvulsant Activity", J. Med. Chem., vol. 11, No. 3, pp. 603–606 (1968).

* cited by examiner

FUSED HETEROCYCLIC COMPOUNDS AND ANALOGS THEREOF, MODULATORS OF NUCLEAR HORMONE RECEPTOR FUNCTION

This application claims priority from provisional U.S. application Ser. No. 60/341,962, filed Dec. 19, 2001, incorporated herein by reference in its entirety.

This application is related to U.S. patent application Ser. No. 10/322,077, filed Dec. 18, 2002, and U.S. patent application Ser. No. 10/322,306, filed Dec. 18, 2002, both of which have common inventors herewith and are assigned to the present assignee.

FIELD OF THE INVENTION

The present invention relates to fused cyclic compounds, to methods of using such compounds in the treatment of nuclear hormone receptor-associated conditions such as cancer, and to pharmaceutical compositions containing such compounds.

BACKGROUND OF THE INVENTION

Nuclear hormone receptors (NHR's) constitute a large super-family of ligand-dependent and sequence-specific transcription factors. Members of this family influence transcription either directly, through specific binding to the promoter target genes (Evans, in *Science* 240: 889–895 (1988)), or indirectly, via protein-protein interactions with other transcription factors (Jonat et al., *Cell* 62: 1189–1204 (1990), Schuele et al., *Cell* 62: 1217–1226 (1990), and Yang-Yen et al., *Cell* 62: 1205–1215 (1990)). The nuclear hormone receptor super-family (also known in the art as the "steroid/thyroid hormone receptor super-family") includes receptors for a variety of hydrophobic ligands, including cortisol, aldosterone, estrogen, progesterone, testosterone, vitamine D3, thyroid hormone and retinoic acid (Evans, 1988, supra). In addition to these conventional nuclear hormone receptors, the super-family contains a number of proteins that have no known ligands, termed orphan nuclear hormone receptors (Mangelsdorf et al., *Cell* 83: 835–839 (1995), O'Malley et al., *Mol. Endocrinol.* 10: 1293 (1996), Enmark et al., *Mol. Endocrinol.* 10, 1293–1307 (1996) and Giguere, *Endocrin. Rev.* 20, 689–725 (1999)). The conventional nuclear hormone receptors are generally transactivators in the presence of ligand, and can either be active repressors or transcriptionally inert in the absence of ligand. Some of the orphan receptors behave as if they are transcriptionally inert in the absence of ligand. Others, however, behave as either constitutive activators or repressors. These orphan nuclear hormone receptors are either under the control of ubiquitous ligands that have not been identified, or do not need to bind ligand to exert these activities.

In common with other transcription factors, the nuclear hormone receptors have a modular structure, being comprised of three distinct domains: an N-terminal domain of variable size containing a transcriptional activation function AF-1, a highly conserved DNA binding domain and a moderately conserved ligand-binding domain. The ligand-binding domain is not only responsible for binding the specific ligand but also contains a transcriptional activation function called AF-2 and a dimerisation domain (Wurtz et al., *Nature Struc. Biol.* 3, 87–94 (1996), Parker et al., *Nature Struc. Biol.* 3, 113–115 (1996) and Kumar et al., *Steroids* 64, 310–319 (1999)). Although the overall protein sequence of these receptors can vary significantly, all share both a common structural arrangement indicative of divergence from an ancestral archetype, and substantial homology (especially, sequence identity) at the ligand-binding domain.

The steroid binding nuclear hormone receptors (SB-NHR's) comprise a sub-family of nuclear hormone receptors. These receptors are related in that they share a stronger sequence homology to one another, particularly in the ligand binding domain (LBD), than to the other members of the NHR super-family (Evans, 1988, supra) and they all utilize steroid based ligands. Some examples of this sub-family of NHR's are the androgen receptor (AR), the estrogen receptor (ER), the progesterone receptor (PR), the glucocorticoid receptor (GR), the mineralocorticoid receptor (MR), the aldosterone receptor (ALDR) and the steroid and xenobiotic receptor (SXR) (Evans et al., WO 99/35246). Based on the strong sequence homology in the LBD, several orphan receptors may also be members of the SB-NHR sub-family.

Consistent with the high sequence homology found in the LBD for each of the SB-NHR's, the natural ligands for each is derived from a common steroid core. Examples of some of the steroid based ligands utilized by members of the SB-NHR's include cortisol, aldosterone, estrogen, progesterone, testosterone and dihydrotestosterone. Specificity of a particular steroid based ligand for one SB-NHR versus another is obtained by differential substitution about the steroid core. High affinity binding to a particular SB-NHR, coupled with high level specificity for that particular SB-NHR, can be achieved with only minor structural changes about the steroid core (e.g., Waller et al., *Toxicol. Appl. Pharmacol.* 137, 219–227 (1996) and Mekenyan et al., *Environ. Sci. Technol.* 31, 3702–3711 (1997), binding affinity for progesterone towards the androgen receptor as compared to testosterone).

Numerous synthetically derived steroidal and non-steroidal agonists and antagonists have been described for the members of the SB-NHR family. Many of these agonist and antagonist ligands are used clinically in man to treat a variety of medical conditions. RU486 is an example of a synthetic agonist of the PR, which is utilized as a birth control agent (Vegeto et al., *Cell* 69: 703–713 (1992)), and Flutamide is an example of an antagonist of the AR, which is utilized for the treatment of prostate cancer (Neri et al, *Endo.* 91, 427–437 (1972)). Tamoxifen is an example of a tissues specific modulator of the ER function, that is used in the treatment of breast cancer (Smigel, *J. Natl. Cancer Inst.* 90, 647–648 (1998)). Tamoxifen can function as an antagonist of the ER in breast tissue while acting as an agonist of the ER in bone (Grese et al., *Proc. Natl. Acad. Sci. USA* 94, 14105–14110 (1997)). Because of the tissue selective effects seen for Tamoxifen, this agent and agents like it are referred to as "partial-agonist" or partial-antagonist". In addition to synthetically derived non-endogenous ligands, non-endogenous ligands for NHR's can be obtained from food sources (Regal et al., *Proc. Soc. Exp. Biol. Med.* 223, 372–378 (2000) and Hempstock et al., *J. Med. Food* 2, 267–269 (1999)). The flavanoid phytoestrogens are an example of an unnatural ligand for SB-NHR's that are readily obtained from a food source such as soy (Quella et al., *J. Clin. Oncol.* 18, 1068–1074 (2000) and Banz et al., *J. Med. Food* 2, 271–273 (1999)). The ability to modulate the transcriptional activity of individual NHR by the addition of a small molecule ligand, makes them ideal targets for the development of pharmaceutical agents for a variety of disease states.

As mentioned above, non-natural ligands can be synthetically engineered to serve as modulators of the function of NHR's. In the case of SB-NHR's, engineering of an unnatural ligand can include the identification of a core structure which mimics the natural steroid core system. This can be achieved by random screening against several SB-NHR's or through directed approaches using the available crystal structures of a variety of NHR ligand binding domains (Bourguet et al., *Nature* 375, 377–382 (1995), Brzozowski, et al., *Nature* 389, 753–758 (1997), Shiau et al., *Cell* 95, 927–937 (1998) and Tanenbaum et al., *Proc. Natl. Acad. Sci. USA* 95, 5998–6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHR in *J. Med. Chem.*, 41, 623 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

The compounds of the present invention comprise a core which serves as a steroid mimic, and are useful as modulators of the function of steroid binding nuclear hormone receptors, as well as other NHR as described following.

SUMMARY OF THE INVENTION

The present invention provides fused cyclic compounds of the following formula I and salts thereof, which compounds are especially useful as modulators of nuclear hormone receptor function:

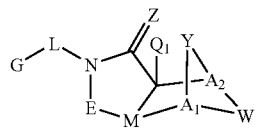

I

As used in formula I, and throughout the specification, the symbols have the following meanings unless otherwise indicated, and are, for each occurrence, independently selected:

G is an aryl or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, $R^1OC=O$, $R^1C=O$, $R^1C=S$, $R^1HNC=O$, $R^1R^2NC=O$, $HOCR^3R^{3'}$, nitro, $R^1OCH_2$, $R^1O$, $NH_2$, $NR^4R^5$, $SR^1$, $S=OR^1$, $SO_2R^1$, $SO_2OR^1$, $SO_2NR^1R^{1'}$, $(R^1O)(R^{1'}O)P=O$, oxo, $(R^1)(R^{1'})P=O$, or $(R^{1'})(NHR^1)P=O$;

Z is O, S, NH, or $NR^6$;

E and M are selected such that:
(i) E is S, SO, $SO_2$, NH, $NR^7$ or $CR^7R^{7'}$ and M is C-$Q_2$; or
(ii) E is $C=CR^{10}R^{10'}$ and M is N or C-$Q_2$;

$A_1$ is $CR^7$ or N;

$A_2$ is $CR^7$ or N;

Y is J-J'-J" where J is $(CR^7R^{7'})$n and n=0–3, J' is a bond or O, S, S=O, $SO_2$, NH, $NR^7$, C=O, OC=O, $NR^1C=O$, $CR^7R^{7'}$, $C=CR^8R^{8'}$, $R^2P=O$, $R^2P=S$, $R^2OP=O$, $R^2NHP=O$, $OP=OOR^2$, $OP=ONHR^2$, $OP=OR^2$, $OSO_2$, $C=NR^7$, NHNH, $NHNR^6$, $NR^6NH$, N=N, cycloalkyl or substituted cycloalkyl, cycloalkenyl or substituted cycloalkenyl, heterocyclo or substituted heterocyclo or aryl or substituted aryl, and J" is $(CR^7R^{7'})$n and n=0–3, where Y is not a bond (i.e., if J' is a bond, then in at least one of J or J" (each defined as $(CR^7R^{7'})$n), n is not zero);

W is $CR^7R^{7'}$—$CR^7R^{7'}$, $CR^8$=$CR^{8'}$, $CR^7R^{7'}$—C=O, $NR^9$—$CR^7R^{7'}$, N=$CR^8$, N=N, $NR^9$—$NR^{9'}$, S—$CR^7R^{7'}$, SO—$CR^7R^{7'}$, $SO_2$—$CR^7R^{7'}$, cycloalkyl or substituted cycloalkyl, cycloalkenyl or substituted cycloalkenyl, heterocyclo or substituted heterocyclo, or aryl or substituted aryl;

$Q_1$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;

$Q_2$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;

L is a bond, $(CR^7R^{7'})$n, NH, $NR^5$, $NH(CR^7R^{7'})$n, or $NR^5(CR^7R^{7'})$n, where n=0–3;

$R^1$ and $R^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl;

$R^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

$R^3$ and $R^{3'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, hydroxylamine, hydroxamide, alkoxy or substituted alkoxy, amino, $NR^1R^2$, thiol, alkylthio or substituted alkylthio;

$R^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C=O$, $R^1NHC=O$, $R^1OC=O$, $SO_2OR^1$, or $SO_2NR^1R^{1'}$;
- $R^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C=O$, $R^1NHC=O$, $SO_2R^1$, $SO_2OR^1$, or $SO_2NR^1R^{1'}$;
- $R^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C=O$, $R^1NHC=O$, $SO_2R^1$, $SO_2OR^1$, or $SO_2NR^1R^{1'}$;
- $R^7$ and $R^{7'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, $N_3$ (i.e., azide), CN, $OR^1$, $O(C=O)R^1$, $O(C=O)NHR^1$, $O(C=O)OR^1$, nitro, hydroxylamine, hydroxylamide, amino, $SR^1$, $SeR^1$, $NHR^4$, $NR^2R^5$, $NOR^1$, thiol, alkylthio or substituted alkylthio, $R^1C=O$, $R^1OC=O$, $R^1NHC=O$, $SO_2R^1$, $SOR^1$, $PO_3R^1R^{1'}$, $R^1R^{1'}NC=O$, $C=OSR^1$, $SO_2R^1$, $SO_2OR^1$, $SO_2NR^1R^{1'}$, $OSO_2$-aryl, $OSO_2$-(substituted aryl), $OSO_2$-heterocyclo, $OSO_2$-(substituted heterocycle), or COCl;
- $R^8$ and $R^{8'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, $OR^1$, amino, $NHR^4$, $NR^2R^5$, $NOR^1$, alkylthio or substituted alkylthio, $C=OSR^1$, $R^1OC=O$, $R^1C=O$, $R^1NHC=O$, $R^1R^{1'}NC=O$, $SO_2OR^1$, $S=OR^1$, $SO_2R^1$, $PO_3R^1R^{1'}$, or $SO_2NR^1R^{1'}$;
- $R^9$ and $R^{9'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C=O$, $R^1OC=O$, $R^1NHC=O$, $SO_2OR^1$, or $SO_2NR^1R^{1'}$; and
- $R^{10}$ and $R^{10'}$ are each independently H, $R^1$, $COOR^1$, $CONR^1R^2$, halo (i.e., Cl, F, Br, I), CN, $OR^1$, $R^1C=O$, $SO_2OR^1$, or $SO_2NR^1R^{1'}$.

Compounds within formula I are novel, a preferred subgenus of which is the following formula Ia and salts thereof:

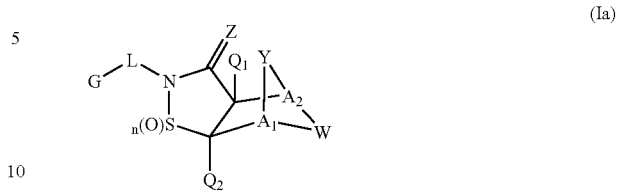

(Ia)

where G, Y, W, $Q_1$ and $Q_2$ are as defined above;

$A_1$ is $CR^7$;

$A_2$ is $CR^7$;

n=1–2;

Z is O; and

L is a bond.

Another preferred subgenus is the following formula Ib and salts thereof:

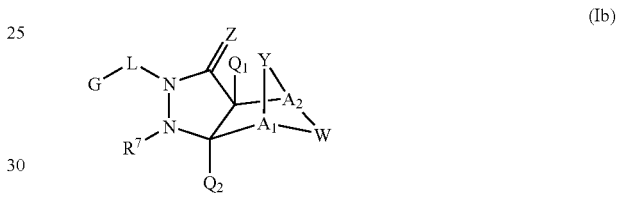

(Ib)

where G, W, Y, $R^7$, $Q_1$ and $Q_2$ are as defined above;

$A_1$ is $CR^7$;

$A_2$ is $CR^7$;

Z is O; and

L is a bond.

Another preferred subgenus is the following formula Ic and salts thereof:

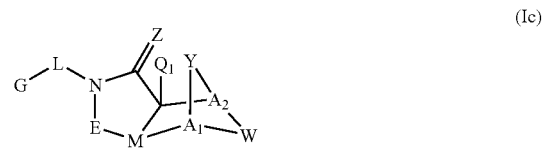

(Ic)

where G, W, and $Q_1$ are as defined above;

E is $C=CR^{10}R^{10'}$, and M is N or C-$Q_2$ where $Q_2$ is as defined above;

Y is J-J'-J" where J is $(CR^7R^{7'})n$ and n=0–3, J' is a bond or $C=O$, $CR^7R^{7'}$, $C=CR^8R^{8'}$, cycloalkyl or substituted cycloalkyl, cycloalkenyl or substituted cycloalkenyl, heterocyclo or substituted heterocyclo or aryl or substituted aryl, and J" is $(CR^7R^{7'})n$ and n=1–3;

$R^{10}$ and $R^{10'}$ are each independently H, $R^1$, $COOR^1$, $CONR^1R^2$, Cl, F, Br, I, CN, $OR^1$, $R^1C=O$, $SO_2OR^1$, or $SO_2NR^1R^{1'}$;

$A_1$ is $CR^7$;

$A_2$ is $CR^7$;

Z is O;

L is a bond.

Another preferred subgenus is the following formula Id and salts thereof:

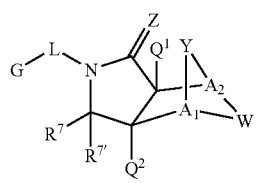

(Id)

where G, Y, W, R$^7$, R$^{7'}$, Q$_1$ and Q$_2$ are as defined above;
A$_1$ is CR$^7$;
A$_2$ is CR$^7$;
Z is O; and
L is a bond.
with the proviso that when A$_1$ and A$_2$ are CH; Y is O, CH$_2$ or NH; W is CH$_2$—CH$_2$ or CH═CH; Q$^2$ is H or CH$_2$OH; and Q$_1$ is H or CH$_2$OH, then (i) G-L is not pyridinyl, phenyl, dichlorophenyl, bromophenyl or methoxyphenyl when E is CH(OH) or CH(OCH$_3$) and (ii) G-L is not methoxyphenyl or phenyl substituted with —OCH$_2$CH$_2$-SB where SB is dimethylamino, diethylamino, piperidinyl, morpholinyl, or pyrrolidinyl when E is CH$_2$.

Preferably, compounds of formula I are monomeric, and are not comprised within other oligomers or polymers.

The compounds of formula I and salts thereof comprise a core which can serve as a steroid mimic (and do not require the presence of a steroid-type (e.g., cyclopentanoperhydrophenanthrene analog) structure).

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary such groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include but are not limited to one or more of the following groups: halo (e.g., a single halo substituent or multiple halo substitutents forming, in the latter case, groups such as a perfluoroalkyl group or an alkyl group bearing Cl$_3$ or CF$_3$), alkoxy, alkylthio, hydroxy, carboxy (i.e., —COOH), alkoxycarbonyl, alkylcarbonyloxy, amino (i.e., —NH$_2$), carbamoyl or substituted carbomoyl, carbamate or substituted carbamate, urea or substituted urea, amidinyl or substituted amidinyl, thiol (i.e., —SH), aryl, heterocycle, cycloalkyl, heterocycloalkyl, —S-aryl, —S-heterocycle, —S═O-aryl, —S═O-heterocycle, arylalkyl-O—, —S(O)$_2$-aryl, —S(O)$_2$-heterocycle, —NHS(O)$_2$-aryl, —NHS(O)$_2$-heterocycle, —NHS(O)$_2$NH-aryl, —NHS(O)$_2$NH-heterocycle, —P(O)$_2$-aryl, —P(O)$_2$-heterocycle, —NHP(O)$_2$-aryl, —NHP(O)$_2$-heterocycle, —NHP(O)$_2$NH-aryl, —NHP(O)$_2$NH-heterocycle, —O-aryl, —O-heterocycle, —NH-aryl, —NH-heterocycle, —NHC═O-aryl, —NHC═O-alkyl, —NHC═O-heterocycle, —OC═O-aryl, —OC═O-heterocycle, —NHC═ONH-aryl, —NHC═ONH-heterocycle, —OC═OO-aryl, —OC═OO-heterocycle, —OC═ONH-aryl, —OC═ONH-heterocycle, —NHC═OO-aryl, —NHC═OO-heterocycle, —NHC═OO-alkyl, —C═ONH-aryl, —C═ONH-heterocycle, —C═OO-aryl, —C═OO-heterocycle, —N(alkyl)S(O)$_2$-aryl, —N(alkyl)S(O)$_2$-heterocycle, —N(alkyl)S(O)$_2$NH-aryl, —N(alkyl)S(O)$_2$NH-heterocycle, —N(alkyl)P(O)$_2$-aryl, —N(alkyl)P(O)$_2$-heterocycle, —N(alkyl)P(O)$_2$NH-aryl, —N(alkyl)P(O)$_2$NH-heterocycle, —N(alkyl)-aryl, —N(alkyl)-heterocycle, —N(alkyl)C═O-aryl, —N(alkyl)C═O-heterocycle, —N(alkyl)C═ONH-aryl, —N(alkyl)C═ONH-heterocycle, —OC═ON(alkyl)-aryl, —OC═ON(alkyl)-heterocycle, —N(alkyl)C═OO-aryl, —N(alkyl)C═OO-heterocycle, —C═ON(alkyl)-aryl, —C═ON(alkyl)-heterocycle, —NHS(O)$_2$N(alkyl)-aryl, —NHS(O)$_2$N(alkyl)-heterocycle, —NHP(O)$_2$N(alkyl)-aryl, NHP(O)$_2$N(alkyl)-heterocycle, —NHC═ON(alkyl)-aryl, —NHC═ON(alkyl)-heterocycle, —N(alkyl)S(O)$_2$N(alkyl)-aryl, —N(alkyl)S(O)$_2$N(alkyl)-heterocycle, —N(alkyl)P(O)$_2$N(alkyl)-aryl, —N(alkyl)P(O)$_2$N(alkyl)-heterocycle, —N(alkyl)C═ON(alkyl)-aryl, and —N(alkyl)C═ON(alkyl)-heterocycle. In the aforementioned exemplary substitutents, in each instance, groups such as "alkyl", "aryl" and "heterocycle" can themselves be optionally substituted; for example, "alkyl" in the group "NCH═OO-alkyl" recited above can be optionally substituted so that both "NHC═OO-alkyl" and "NHC═OO-substituted alkyl" are exemplary substituents.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkenyl or substituted cycloalkenyl.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkyl or substituted cycloalkyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively.

The term "alkoxycarbonyl" refers to an alkoxy group bonded through a carbonyl group.

The term "alkylcarbonyl" refers to an alkyl group bonded through a carbonyl group. The term "alkylcarbonyloxy" refers to an alkylcarbonyl group bonded through an oxygen linkage.

The terms "arylalkyl", "substituted arylalkyl," "cycloalkylalkyl," "substituted cycloalkylalkyl," "cycloalkenylalkyl", "substituted cycloalkenylalkyl", "heterocycloalkyl" and "substituted heterocycloalkyl" refer to aryl, cycloalkyl, cycloalkenyl and heterocyclo groups bonded through an alkyl group, substituted on the aryl, cycloalkyl, cycloalkenyl or heterocyclo and/or the alkyl group where indicated as "substituted."

The term "aryl" refers to cyclic, aromatic hydrocarbon groups which have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1,2,3,4 or 5 substituents, at any point of attachment. Exemplary substituents include, but are not limited to, nitro, cycloalkyl or substituted cycloalkyl, cycloalkenyl or substituted cycloalkenyl, cyano, alkyl-$S(O)_m$— (m=0, 1 or 2), alkyl or substituted alkyl, as well as those groups recited above as exemplary alkyl substituents and as previously mentioned as preferred aryl substituents in the definition for G. Exemplary substituents also include fused cyclic substituents, such as heterocyclo or cycloalkenyl, or substituted heterocyclo or cycloalkenyl, groups (e.g., thereby forming a fluoroenyl, tetrahydronapthalenyl, or dihydroindenyl group).

"Carbamoyl" refers to the group —CONH— which is bonded on one end to the remainder of the molecule and on the other to hydrogen or an organic moiety (such as alkyl, substituted alkyl, aryl, substituted aryl, heterocycle, alkylcarbonyl, hydroxyl and substituted nitrogen). "Carbamate" refers to the group —O—CO—NH— which is bonded on one end to the remainder of the molecule and on the other to hydrogen or an organic moiety (such as those listed above). "Urea" refers to the group —NH—CO—NH— which is bonded on one end to the remainder of the molecule and on the other to hydrogen or an organic moiety (such as those listed above). "Amidinyl" refers to the group —C(=NH)(NH$_2$). "Substituted carbamoyl," "substituted carbamate," "substituted urea" and "substituted amidinyl" refer to carbamoyl, carbamate, urea or amidinyl groups as described above in which one more of the hydrogen groups are replaced by an organic moiety (such as those listed above).

The terms "heterocycle", heterocyclic" and "heterocyclo" refer to fully saturated, or partially or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic, heterocyclic groups include carbazolyl, benzidolyl, phenanthrolinyl, dibenzofuranyl, acridinyl, phenanthridinyl, xanthenyl and the like.

"Substituted heterocycle," "substituted heterocyclic," and "substituted heterocyclo" (such as "substituted heteroaryl") refer to heterocycle, heterocyclic or heterocyclo groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl-$S(O)_m$— (m=0, 1 or 2), alkyl or substituted alkyl, as well as those groups recited above as exemplary alkyl substituents, and as previously mentioned as preferred heterocyclo substituents in the definition for G.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The terms "halogen" or "halo" refer to chlorine, bromine, fluorine or iodine.

The terms "hydroxylamine" and "hydroxylamide" refer to the groups OH—NH— and OH—NH—CO—, respectively.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

When a term such as "(CRR)n" is used, it denotes an optionally substituted alkyl chain existing between the two fragments to which it is bonded, the length of which chain is defined by the range described for the term n. An example of this is n=0–3, implying from zero to three (CRR) units existing between the two fragments, which are attached to the primary and terminal (CRR) units. In the situation where the term n is set to zero (n=0) then a bond exists between the two fragments attached to (CRR).

Unless otherwise indicated, any heteroatom with unsatisfied valences is assumed to have hydrogen atoms sufficient to satisfy the valences.

Divalent groups, such as those in the definition of W (e.g., $NR^9$—$CR^7R^{7'}$), may be bonded in either direction to the remainder of the molecule (e.g,

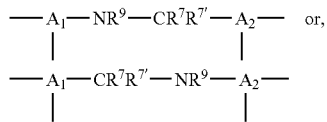

for the aforementioned group within the definition of W).

Carboxylate anion refers to a negatively charged group —COO$^-$.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings. In certain cases, for example, the exo or endo conformation can be preferred for the fused ring system bonded to G-L in formula I. For example, for androgen receptor antagonists (or selective androgen receptor modulators), where Y is O or NR[7], the exo configuration can be preferred, while for most other definitions of Y, the endo configuration can be preferred. As can be appreciated, the preferred configuration can be a function of the particular compound and its preferred activity. Separation of configurational isomers can be achieved by any suitable method, such as column chromatography.

Throughout the specifications, groups and substituents thereof may be chosen to provide stable moieties and compounds.

Embodiments indicated herein as exemplary or preferred are intended to be illustrative and not limiting.

Methods of Preparation

The compounds of the present invention may be prepared by methods such as those illustrated in the following Schemes I to XXII. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques. See the following which describe other methods which may be employed in the preparation of compounds of the present invention: Li, et al., *Eur. J. Org. Chem.* 9, 1841–1850 (1998); Li, Y-Q, *Synlett.* 5, 461–464 (1996); Thiemann, et al., *Bull. Chem. Soc. Jpn.* 67, 1886–1893 (1994); Tsuge et al., *Heterocycles* 14, 423–428 (1980); Ward et al., *Can J. Chem.* 75, 681–693 (1997); Ward et al., *Can J. Chem.* 69, 1487–1497 (1991); Ward et al., *Tetrahedron Lett.* 31, 845–848 (1990); Fleming et al., *J. Org. Chem.* 44, 2280–2282 (1979); Jankowski et al., *J. Organomet. Chem.* 595, 109–113 (2000); Keglevich et al., *J. Organomet. Chem.* 579, 182–189 (1999); Keglevich et al., *J. Organomet. Chem.* 570, 49–539 (1998); Jankowski et al., *Hetroat. Chem.* 7, 369–374 (1996); Jankowski et al., *J. Am. Chem. Soc.* 113, 7011–7017 (1991); Quin et al., *Tetrahedron Lett.* 31, 6473–6476 (1990); Quin et al., *J. Org. Chem.* 59, 120–129 (1994); Quin et al., *J. Org. Chem.* 58, 6212–6216 (1993); Quin et al., *Phosphorous, Sulfur Silicon Relat. Elem.* 63, 349–362 (1991); Quin et al., *Hetroat. Chem.* 2, 359–367 (1991); Hussong et al., *Phosphorus Sulfur.* 25, 201–212 (1985); Quin et al., *J. Org. Chem.* 51, 3341–3347 (1986); Myers et al., *J. Am. Chem. Soc.* 114, 5684–5692 (1992); Myers et al., *J. Am. Chem. Soc.* 113, 6682–6683 (1991); Shen et al., U.S. Pat. No. 5,817,679; Cordone et al., *J. Am. Chem. Soc.* 111, 5969–5970 (1989); Jung et al., *J. Chem. Soc. Commun.* 630–632 (1984); Lay et al., *J. Am. Chem. Soc.* 104, 7658–7659 (1982); Gonzalez et al., *J. Am. Chem. Soc.* 117, 3405–3421 (1995); Kreher et al., *Chem Ber.* 125, 183–189 (1992); Simig et al., *Synlett.* 7, 425–426 (1990); Sha et al., *J. Org. Chem.* 55, 2446–2450 (1990); Drew et al., *J. Chem. Soc., Perkin Trans.* 1 7, 1277–1284 (1985); Kreher et al., *Anorg. Chem., Org Chem.* 31B, 599–604 (1976); Avalos et al., *Tetrahedron Lett.* 39, 9301–9304 (1998); Gousse et al., *Macromolecules* 31, 314–321 (1998); Mikhailyuchenko et al., *Khim. Geterotsikl. Soedin.* 6, 751–758 (1993); Lubowitz et al., U.S. Pat. No. 4,476,184; Padwa et al., *J. Org. Chem.* 61, 3706–3714 (1996); Schlessinger et al., *J. Org. Chem.* 59, 3246–3247 (1994); Buchmeiser et al., WO Publication No. 9827423; Tanabe et al., Japanese Patent Document JP 07144477; Mochizucki et al., Japanese Patent Document JP 63170383; Hosoda et al., Japanese Patent Document JP 62053963; Onaka et al., Japanese Patent Document JP 62053964; Kato et al., Japanese Patent Document JP 53086035; Kato et al., Japanese Patent Document JP 51088631; Tottori et al., Japanese Patent Document JP 49124225; Augustin et al., German Patent Document DD101271; Title et al., French Patent Document FR 2031538; Gousse et al., *Polym. Int.* 48, 723–731 (1999); Padwa et al., *J. Org. Chem.* 62, 4088–4096 (1997); Theurillat-Moritz et al., *Tetrahedron: Asymmetry* 7, 3163–3168 (1996); Mathews et al., *J. Carbohydr. Chem.* 14, 287–97 (1995); Srivastava et al., *Natl. Acad. Sci. Lett. (India)* 15, 41–44 (1992); Mayorga et al., *Rev. Cubana Quim.* 4, 1–6 (1988); Kondoli et al., *J. Chem. Res., Synop.* 3, 76 (1987); Primelles et al., *Cent. Azucar* 7–14 (1985); Solov'eva et al., *Khim. Geterotsikl. Soedin.* 5, 613–15 (1984); Liu et al., *Yaoxue Xuebao* 18, 752–759 (1983); Joshi et al., *Indian J. Chem, Sect. B.* 22B, 131–135 (1983); Amos et al., WO Publication No. 9829495; Odagiri et al., U.S. Pat. No. 4,670,536; Gallucci et al., European Patent Document EP 355435; Redmore, D. U.S. Pat. No. 3,821,232; Nakano et al., *Heterocycles* 35, 37–40 (1993); Tomisawa et al., *Chem. Pharm. Bull.* 36, 1692–1697 (1988); Krow et al., *J. Heterocycl. Chem.* 22, 131–135 (1985); Krow et al., *J. Org. Chem.* 47, 1989–1993 (1982); Liu et al., *Yaoxue Xuebao* 18, 752–759 (1983); Nishikawa et al., *Yaoxue Xuebao* JP 01061457; and/or Rice et al., *J. Med. Chem.* 11, 183–185 (1968).

All documents cited in the present specification, such as those cited in this "Methods of Preparation" as well as other sections herein, are incorporated herein by reference in their entirety including, but not limited to, U.S. application Ser. No. 09/885,798, U.S. application Ser. No. 09/885,381 and U.S. application Ser. No. 60/271,672. Reference to any document herein is not to be construed as an admission that such document is prior art.

Scheme I

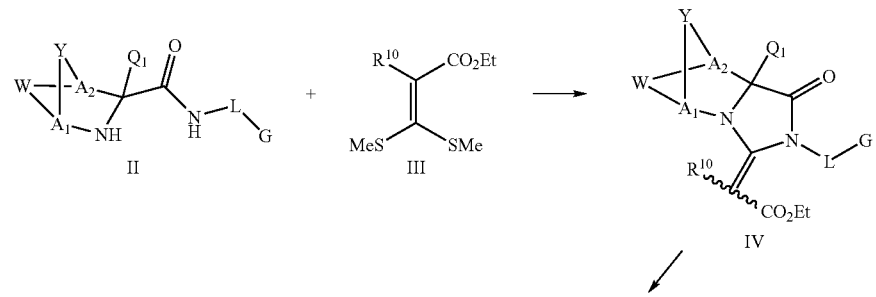

-continued

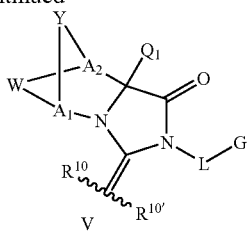

$R^{10'}$ = COOR$^1$, CN or CONR$^1$R$^2$

Imidazolinones of formulas IV and V, which are compounds of formula I, are prepared as illustrated in Scheme I. The intermediates of formula II (which can be synthesized as described in U.S. application Ser. No. 09/885,798) are treated with ketene dithioacetals of formula III to form imidazolinones of formula IV. The reaction occurs, for example, in the presence of triethylamine or sodium methoxide/ethoxide in ethanol or methanol at reflux according to the procedure outlined by Huang et al., *Synth. Commun.* 21, 1177–1187 (1991). The ketene dithioacetals of formula III are commercially available or can be prepared by one skilled in the art.

The ester group in compounds of formula IV can be hydrolyzed, for example, with sodium hydroxide in solvents such as methanol or ethanol at about 0° C. to 50° C. to provide the corresponding carboxylic acid. The acid can be converted to the corresponding ester ($R^{10'}$=COOR$^1$) or the amide ($R^{10'}$=CONR$^1$R$^2$) of formula V by treatment with thionyl, chloride or oxalyl chloride to form the acid chloride followed by treatment with the appropriate alcohol R$^1$—OH or amine H—NR$^1$R$^2$ respectively.

Treatment of the acid chloride with ammonia produces the unsubstituted amide, $R^{10'}$=CONH$_2$, which can be dehydrated by conventional methods to form the nitrile, $R^{10'}$=CN.

therein: Hofman et al., *J. Agric. Food Chem.* 45, 898–906 (1997); Baciocchi et al., *J. Chem. Soc., Perkin Trans.* 2 8, 821–824 (1975); Wu et al., *J. Heterocycles* 38, 1507–1518 (1994); Yin et al., *Tetrahedron Lett.* 38, 5953–5954 (1997); Mic'ovic' et al., *Tetrahedron* 20, 2279–2287 (1964); Gorbunova et al., *J. Org. Chem.* 35, 1557–1566 (1999); Rassu et al., *Chem. Soc. Rev.* 29, 109–118 (2000); Kaberdin et al., *Russ. Chem. Rev.* 68, 765–779 (1999); Barluenga et al., *Aldrichimica Acta* 32, 4–15 (1999); Bogdanowicz-Szwed et al., *Pol. Wiad. Chem.* 52, 821–842 (1998); Casiraghi et al., *Adv. Asymmetric Synth.* 3, 113–189 (1998); and/or Baeckvall et al., *Chem. Rev.* 98, 2291–2312 (1998). An intermediate dienophile of formula VII can be obtained from commercial sources or readily made by one skilled in the art, for example, in accordance with the following literature references and the references found therein: Kato et al., WO-9908679; Seijas et al., EP-648757: Beeley et al., *J. Chem. Soc, Perkin Trans.* 1, 16, 2245–2251 (1994); Walder et al., *Helv. Chem. Acta.* 72, 1435–1443 (1989); JP-56118073 & 56081573; Lewis et al., *J. Heterocycl. Chem.* 8, 571–580 (1971).

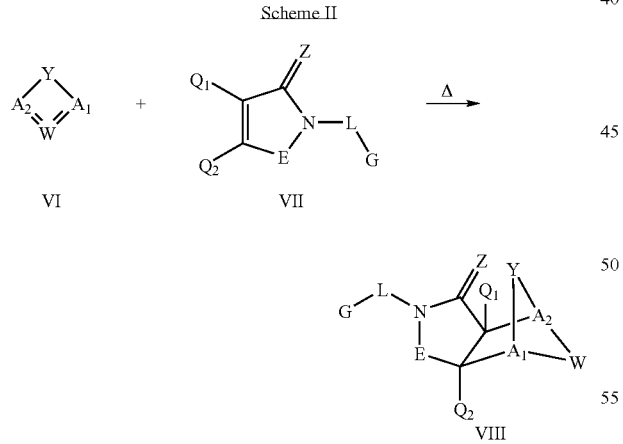

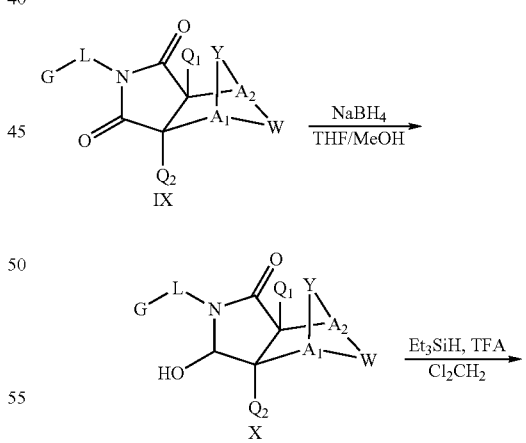

As illustrated in Scheme II, a diene of formula VI can be reacted with a dienophile of formula VII (most preferably, where E is S(O)$_n$), under conditions readily selected by one skilled in the art (such as by the addition of heat ("Δ")), to obtain a compound of formula VIII, which is a compound of formula I. An intermediate diene of formula VI can be obtained from commercial sources or readily made by one skilled in the art, for example, in accordance with the following literature documents and the references found

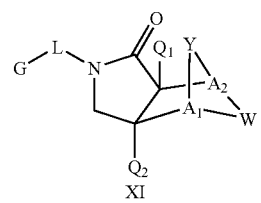

As illustrated in Scheme III, a compound of formula IX can be converted to compounds of formula X and XI, which are compounds of formula I. Treatment of a compound of formula IX with a reducing agent such as NaBH$_4$ in a solvent system such as MeOH and THF, yields an alcohol of formula X. Treatment of a compound of formula X, with a reducing agent such as Et$_3$SiH, results in removal of the hydroxyl group to give a compound of formula XI. Methods for the preparation of intermediates of formula IX are described in U.S. application Ser. Nos. 09/885,381 and 60/271,672 and the documents cited therein, and are incorporated herein.

Scheme IV

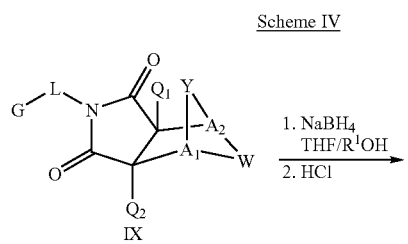

1. NaBH$_4$ THF/R$^1$OH
2. HCl

As illustrated in Scheme IV, a compound of formula IX can be converted to a compound of formula XII, which is a compound of formula I. A compound of formula IX can be treated with a reducing agent such as NaBH$_4$ in a solvent such as THF along with an alcohol of formula R$^1$—OH. After reduction of the imide to the alcohol intermediate (formula X) is complete, the mixture can be treated with an acid such as HCl to yield the ether of formula XII.

Scheme V

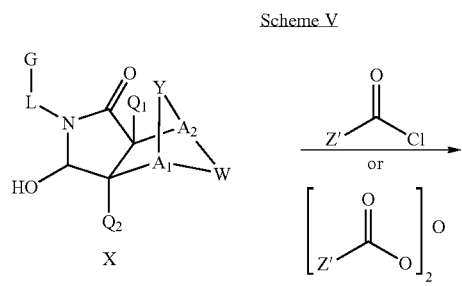

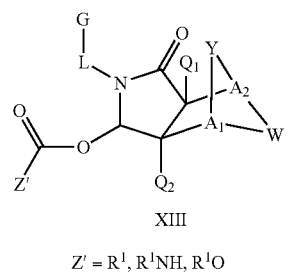

XIII

Z' = R$^1$, R$^1$NH, R$^1$O

As illustrated in Scheme V, a compound of formula X can be converted to a compound of formula XIII, which is a compound of formula I. A compound of formula X can be treated with an acylating agent of formula Z'COCl or anhydride intermediate of formula (Z'COO)$_2$O in the presence of a base such as Et$_3$N, with or without heating, to yield a compound of formula XIII. For compounds of formula XIII, Z' is described as being R$^1$, OR$^1$ or NHR$^1$. Intermediates of formula Z'COCl or (Z'COO)$_2$O can be obtained from commercial sources or can readily be prepared by one skilled in the art.

Scheme VI

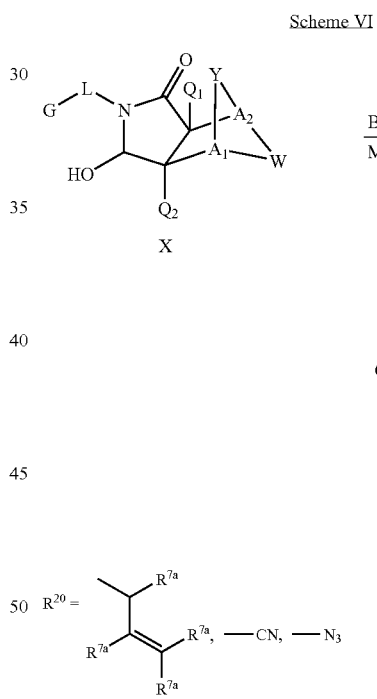

As illustrated in Scheme VI, a compound of formula X can be converted to a compound of formula XIV, which is a compound of formula I. A compound of formula X can be treated with a Lewis acid such as BF$_3$.Et$_2$O and a reagent of formula (R$^1$)$_3$SiR$^{20}$ such as Me$_3$SiR$^{20}$ at a low temperature such as 0° C. to yield a compound of formula XIV. For compounds of formula XIV, R$^{20}$ is described as a substituted allyl group (the groups R$^{7a}$ are independently selected from those groups included in the definition of R$^7$), a nitrile group or an azide group. Intermediates of formula Me$_3$SiR$^{20}$ can be obtained from commercial sources or can readily be prepared by one skilled in the art.

Scheme VII

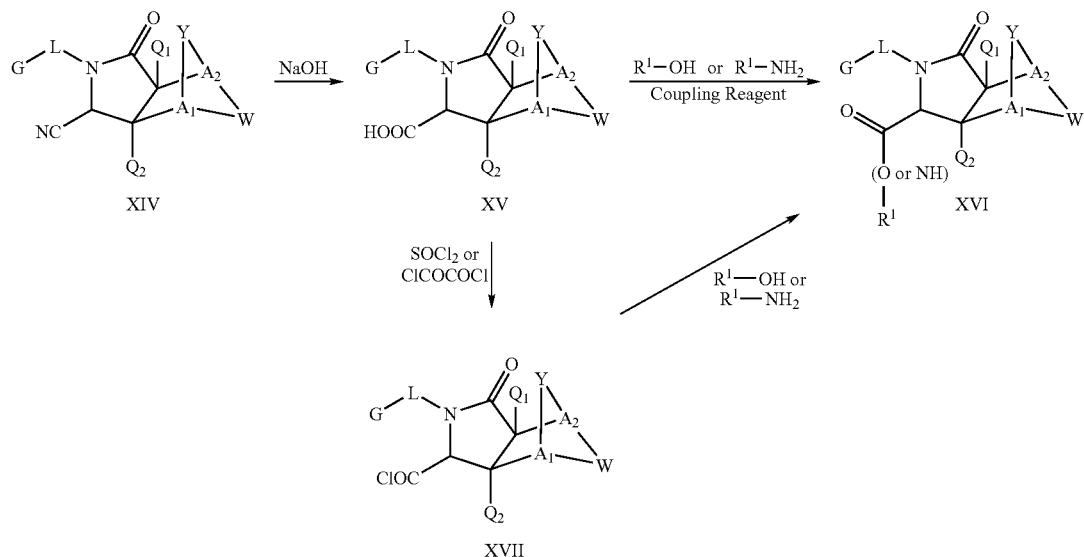

As illustrated in Scheme VII, a compound of formula XIV can be converted to compounds of formula XV, XVI and XVII, which are compounds of formula I. A compound of formula XIV can be treated with an aqueous base such as NaOH, in a manner known to one skilled in the art, to generate a carboxylic acid derivative of formula XV. A compound of formula XV can be treated with intermediates of formula $R^1$—OH or $R^1$—$NH_2$, along with any of an array of different peptide coupling agents well known to one skilled in the art, to generate a compound of formula XVI. Alternatively, a compound of formula XV can be treated with a chlorinating agent such as $SOCl_2$ or ClCOCOCl, in a manner well known to one skilled in the art, to create an acid chloride of formula XVII. A compound of formula XVII can be treated with intermediates of formula $R^1$—OH or $R^1$—$NH_2$ along with a base such as $Et_3N$, with or without base or heating, to generate a compound of formula XVI. Intermediates of formula $R^1$—OH or $R^1$—$NH_2$ can be obtained from commercial sources or prepared by one skilled in the art.

Scheme VIII

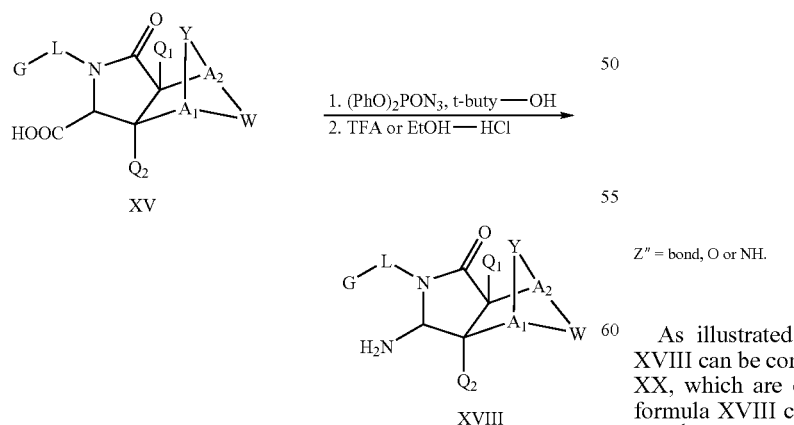

As illustrated in Scheme VIII, a compound of formula XV can be converted to a compound of formula XVIII, which is a compound of formula I. A compound of formula XV can be treated with a reagent such as $(PhO)_2PON_3$ and an alcohol such as t-butyl alcohol to yield a t-butyl carbamate intermediate which can subsequently be deprotected by treatment with acids such as TFA or ethanolic-HCl to yield the free amine compound of formula XVIII.

Scheme IX

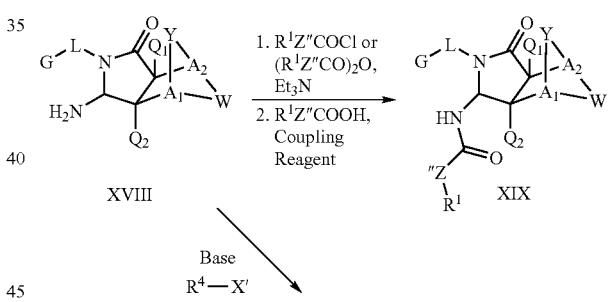

$Z'' =$ bond, O or NH.

As illustrated in Scheme IX, a compound of formula XVIII can be converted to compounds of formulae XIX and XX, which are compounds of formula I. A compound of formula XVIII can be treated with an acylating agent such as $R^1Z''COCl$ or $(R^1Z''CO)_2O$, with a base such as $Et_3N$, with or without heating, in a manner known to one skilled in the art, to generate a compound of formula XIX. Alternatively, a compound of formula XVIII can be treated with an acid of formula R¹Z"COOH along with any of an array of peptide coupling reagents well known to one skilled in the art, to generate a compound of formula XIX. A compound of formula XVIII can also be treated with an alkyl halide of formula R⁴—X' (X'=halo; R⁴ is not (un)substituted aryl or heteroaryl), in the presence of a base such as K₂CO₃ or NaH, to yield an alkyl amine derivative of formula XX. Intermediates of R⁴—X' can be obtained from commercial sources or prepared by one skilled in the art.

Scheme X

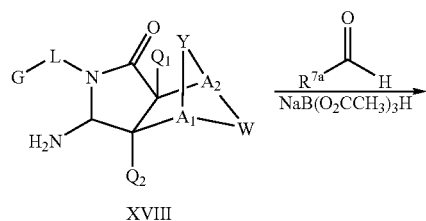

XVIII

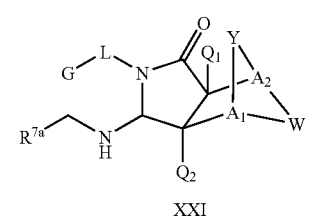

XXI

As illustrated in Scheme X, a compound of formula XVIII can be converted to a compound of formula XXI, which is a compound of formula I. A compound of formula XVIII can be treated with an aldehyde intermediate of formula R⁷ᵃCHO, followed by a reducing agent such as NaB(O₂CCH₃)₃H, in a manner known to one skilled in the art, to yield a compound of formula XXI. Intermediates of R⁷ᵃCHO can be obtained from commercial sources or prepared by one skilled in the art.

Scheme XI

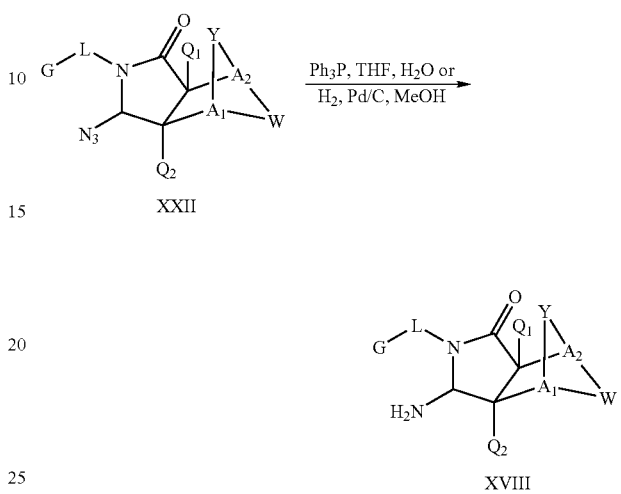

XXII

XVIII

As illustrated in Scheme XI, an alternative route to the formation of a compound of formula XVIII can be achieved through an azide compound of formula XXII. A compound of formula XXII can be derived from the routes described in Scheme VI. Treatment of a compound of formula XXII with a reducing agent such as triphenylphosphine in THF and water or H₂ with catalytic Pd/C in MeOH will give a compound of formula XVIII, which is a compound of formula I.

Scheme XII

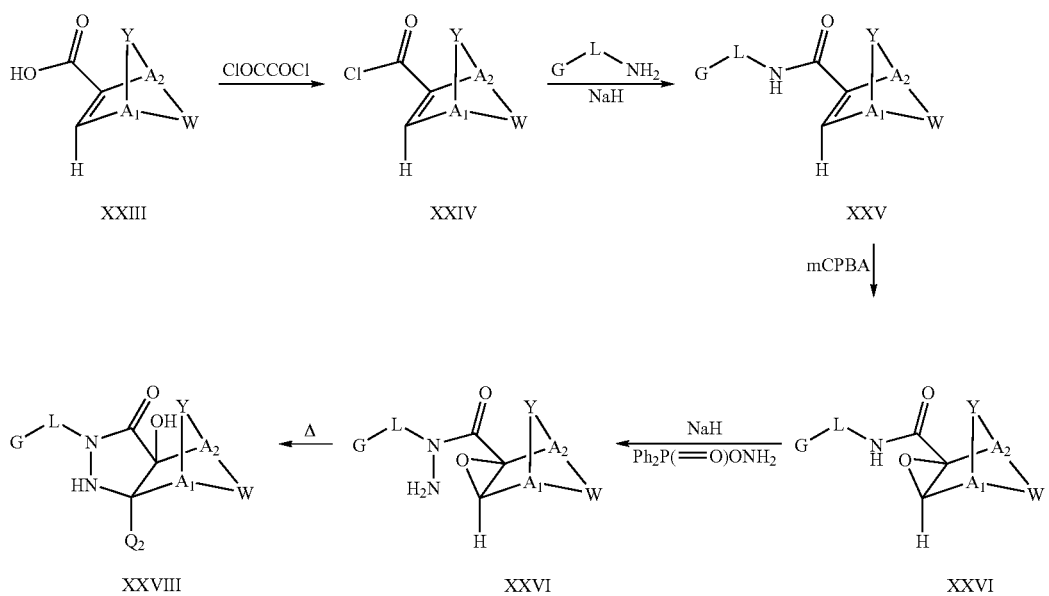

Scheme XII demonstrates the route to the synthesis of compounds of formula XXVIII, which are compounds of formula I. A starting bicyclic intermediate of formula XXIII can be synthesized readily by one skilled in the art as described in the following references and incorporated by reference herein, of Pitha, J. et. al., *J. Med. Chem.* 32, 96–100 (1989); Falck, J. R. et. al., *J. Chem. Soc., Perkin Trans.* 1 2, 413–414 (1990); Baxter, E. W. et. al., *J. Org. Chem.* 54, 2893–2904 (1989); Ried, W. et. al. *Chem. Ber.* 120, 657–658 (1987); Kunng, F.-A. et. al., *J. Org. Chem.* 48, 4262–4266 (1988); Niwayama, S. et. al., *Tetrahedron Lett.* 33, 883–886 (1992); Afarinkia, K. et. al., *Tetrahedron* 55, 3129–3140 (1999); Bates, R. W. et. al., *Aust. J. Chem.* 51, 383–387 (1998); Marko, I. E. et. al., *Tetrahedron Lett.* 34, 7309–7312 (1993); Shimo, T. et. al. *J. Heterocycl. Chem.* 29, 811–813 (1992); Matsui, T. et. al., *Heterocycles* 34, 723–728 (1992); Matsui, T. et. al., *Bull. Chem. Soc. Jpn.* 61, 316–318 (1988); Kvita, V. et. al., *Helv. Chim. Acta.* 68, 1569–1576 (1985); Shiu, L.-H. et. al., *Organometallics* 17, 4206–4212 (1998); Ager, D. J. et. al., *Heterocycles* 37, 1789–1805 (1994); Ager, D. J. et. al., *J. Chem. Res., Synop.* 12, 462–463 (1986); Bock, M., G. et. al., U.S. Pat. No. 5,686,454, Herges, R. et. al., *Chem. Ber.* 127, 1143–1145 (1994); Bock, M. G. et. al., EP 532097, Horton, D. et. al., *Carbohydr. Res.* 216, 33–49 (1991); Chenier, P. J. et. al., *Synth. Commun.* 18, 1947–1959 (1988), Verkruijsse, H. D. et. al., *Recl. Trav. Chim. Pays-Bas* 105, 66–68 (1986); Gupta, I. et. al., *J. Chem. Soc., Chem. Commun.* 21, 1227–1228 (1982); Wilt, J. W. et. al., *J. Org. Chem.* 47, 3721–3730 (1982); Klemarczyk, P. T. et. al., U.S. Pat. No. 4,312,888, Yates, P. et. al., *J. Chem. Soc., Chem. Commun.* 10, 449–451 (1981); Figeys, H. P. et. al., *Tetrahedron Lett.* 21, 2369–2372 (1980); Nallet, J. P. et. al., *Tetrahedron Lett.* 20, 2583–2584 (1979); Rousseau, G. et. al., *Synthesis* 67–70 (1978); Just, G. et. al., *Can. J. Chem.* 54, 2925–2934 (1976); Just, G. et. al., *Can. J. Chem.* 54, 849–950 (1976); Werstiuk, N. H. et. al., *Can. J. Chem.* 53, 26–40 (1975); Mamer, O. A. et. al. *Can. J. Chem.* 52, 1983–1987 (1974); McCoy, L. L. et. al. *J. Am. Chem. Soc.* 95, 7407–7412 (1973); Gassman, P. G. et. al. *J. Am. Chem. Soc.* 90, 1517–1524 (1968); Wilt, J. W. et. al. *J. Org. Chem.* 33, 694–708 (1968). Treatment of a compound of formula XXIII with a chlorinating agent, such as oxalyl chloride, by methods well known to one skilled in the art, yields the acid chloride intermediate of formula XXIV. Treatment of compound XXIV with a base, such as NaH, and an amine intermediate of formula G-L-NH$_2$, in a manner well known to one skilled in the art, yields an amide intermediate of formula XXV. Treatment of a compound of formula XXV with an oxidizing agent such as mCPBA, yields an epoxide intermediate of formula XXVI. Treatment of the intermediate of formula XXVI with an aminating agent such as diphenylphosphinylhydroxylamine, yields a hydrazine intermediate of formula XXVII. Simple heating of the intermediate of formula XXVII results in cyclization via opening of the epoxide to yield a compound of formula XXVIII. Intermediates of formula G-L-NH$_2$ can be obtained from commercial sources or readily synthesized by one skilled in the art.

Scheme XIII

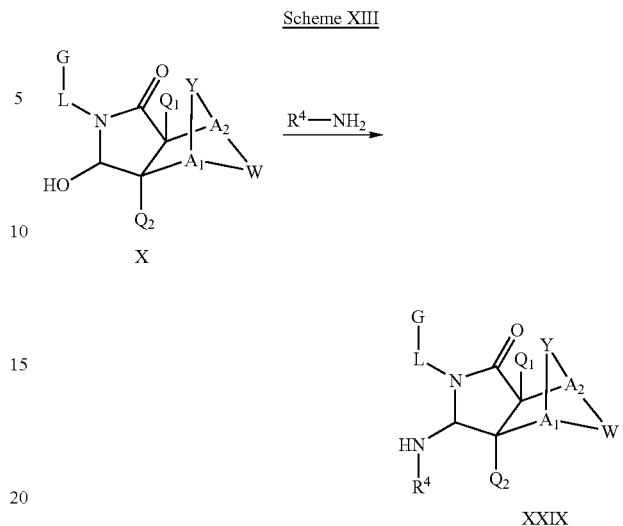

As shown in Scheme XIII, treatment of an alcohol of formula X with an amine of formula R$^4$—NH$_2$, with heating, using methods described in Valters, R. et. al., *Latv. PSR Zinat. Akad. Vestis, Kim. Ser.* 234–237, (1983), will give a substituted amine product of the formula XXIX, which is a compound of formula I.

Scheme XIV

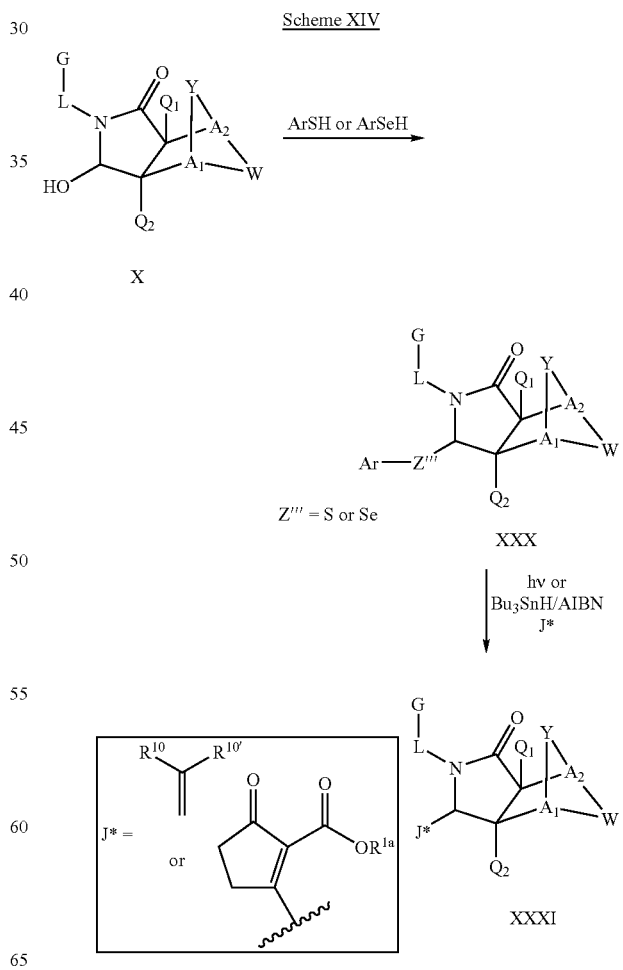

R$^{1a}$ = groups included in the definition of R$^1$.

As shown in Scheme XIV, an alcohol of formula X can be converted to an arylsulfide of formula XXX (Ar=aryl or substituted aryl), which is a compound of formula I, by the methods described in Huang, P. Q. et al., *Tetrahedron Asymm.* 10, 3309–3317, (1999) and Wee, A. G. H. et al. *J. Org. Chem.* 63, 4218–4227 (1998). Alternatively, a phenylselenide compound of formula XXX, for example, can be formed from an alcohol of formula X as described in Kametani, T. et al., *J. Chem. Soc., Perkin Trans.* 1 833–837, (1988). The phenylselenide compound of formula XXX can be irradiated in the presence of a radical acceptor of formula J*, to give a compound of formula XXXI, which is a compound of formula I. The sulfide or the selenide of formula XXX can also be treated with tributyltin hydride in the presence of AIBN (2,2'-azobisisobutyronitrile) and a radical acceptor to give a compound of formula XXXI. A broader description of radical acceptors of formula J* can be found in Giese, B. *Ang. Chem., Int. Ed. Engl.* 22, 753, (1983) and Curran, D. P. *Synthesis* 417, (1988) and are incorporated herein by reference, and are well-known to one skilled in the art.

Scheme XV

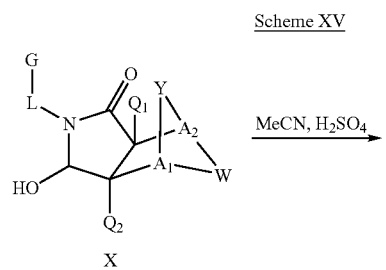

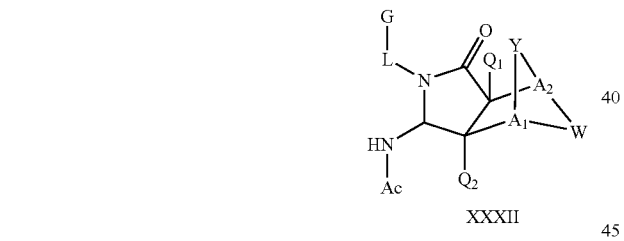

As shown in Scheme XV, treatment of an alcohol of formula X with acetonitrile in sulfuric acid, in a manner described in Nikintin, K. V. et al., *Mendeleev Commun.* 1, 31–32, (2000), will yield a compound of fromula XXXII, which is a compound of formula I.

Scheme XVI

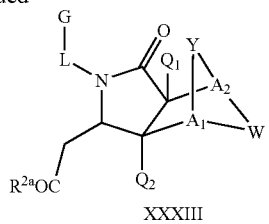

$R^{2a}$ = groups included in the definition of $R^2$.

As shown in Scheme XVI, a compound of formula XXXIII, which is a compound of formula I, can readily be made using methods described in Ishihara, Y. et al., *Chem. Pharm. Bull.* 38, 3024–3030, (1990) and Mali, R. S. et al., *Synthesis* 755–757, (1986). An alcohol of formula X can be reacted with a Wittig reagent, followed by a 1,4-ring closure of the resulting olefin intermediate, to yield a compound of formula XXXIII. The Wittig-type reagents are commercially available or can be synthesized by one skilled in the art.

Scheme XVII

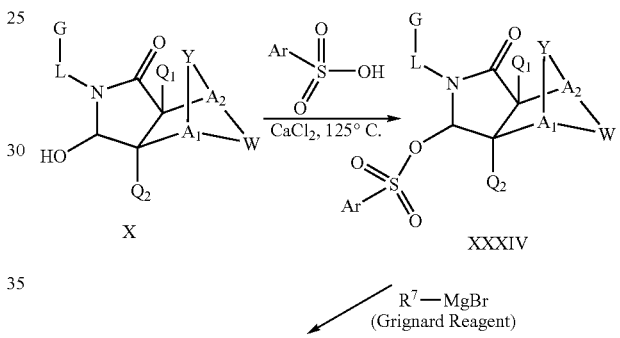

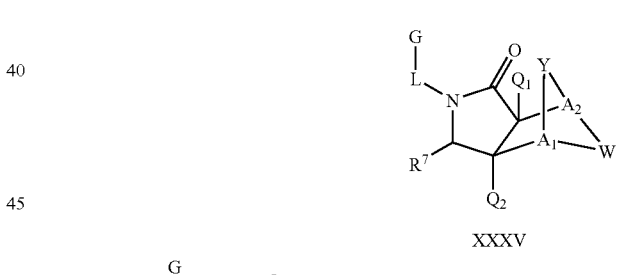

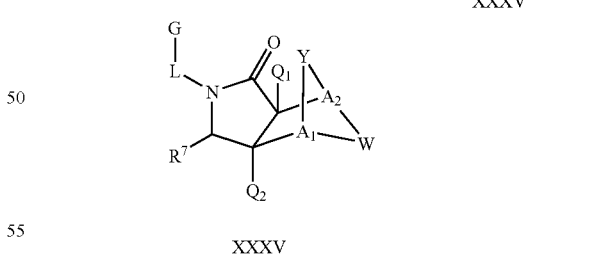

As shown in Scheme XVII, an alcohol of formula X can be reacted with an arylsulfonic acid in the presence of calcium chloride with heating, using methods described in Huang, P. Q. et al., *Synth. Commun.* 30, 2259–2268, (2000), to yield a compound of formula XXXIV, which is a compound of formula I. Arylsulfonic acid intermediates of the type described can be obtained from commercial sources or readily made by one skilled in the art. A compound of formula XXXIV can be reacted with a Grignard reagent, by methods described in Arai, Y. et al., *Chem. Pharm. Bull.* 40,

Scheme XVIII

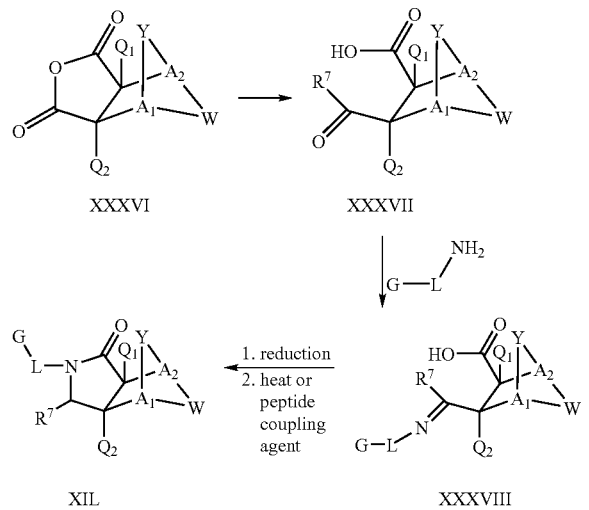

As shown in scheme XVIII, an intermediate of formula XXXVI, which can be made as described in U.S. application Ser. No. 09/885,381 or U.S. application Ser. No. 60/271,672, can be reacted with alkyl or aryl lithium reagents or with alkyl or aryl Grignard reagents as shown in Cornelius, L. A. et al., *J. Org. Chem.* 58, 3188–3190, (1993) and Canonne, P. et al., *Tetrahedron Lett.* 27, 2001–2004, (1986), to yield an intermediate of formula XXXVII. The intermediate ketone of formula XXXVII can then be condensed with an amine of formula G-L-NH$_2$ to give an imine intermediate of formula XXXVIII. The imine intermediate of formula XXXVIII, which need not be isolated, can be reduced by methods well-known to one skilled in the art (or heated, or contacted with a peptide coupling agent), and then cyclized, to give a compound of formula XIL, which is a compound of formula I.

Scheme XIX

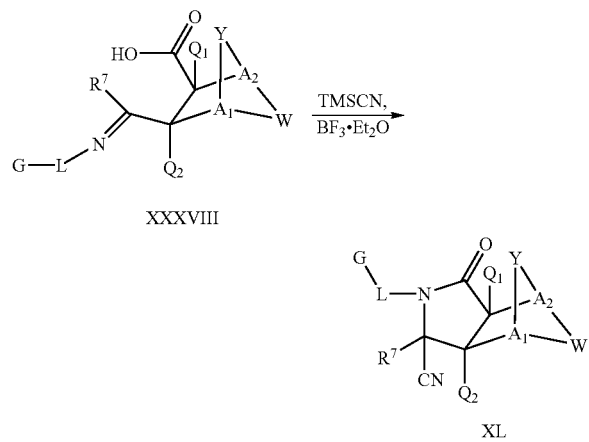

As shown in Scheme XIX, an imine intermediate of formula XXXVIII can be treated with a source of cyanide anion, such as TMSCN, in the presence of a Lewis acid, such as borontrifluoride etherate, using methods described in Kuehling et al., *Chem. Ber.* 23, 709, (1890) and Kuehling et al., *Chem. Ber.* 38, 1222, (1905), to give a compound of formula XL, which is a compound of formula I.

Scheme XX

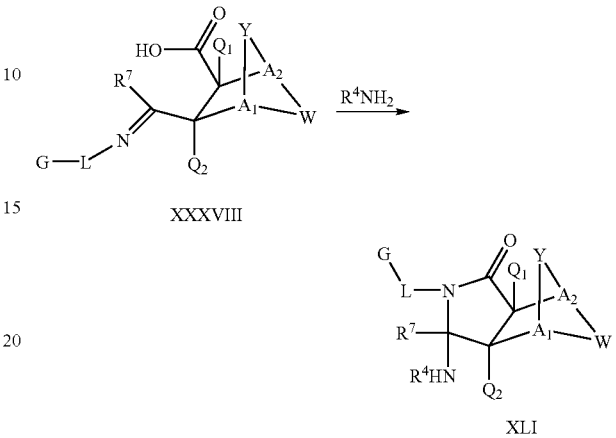

As illustrated in Scheme XX, an imine intermediate of formula XXXVII can be treated with a primary amine of formula R$^4$—NH$_2$, using methods described in Stajer, G. et al., *Heterocycles* 37 883–890, (1994) and Sohar, P. et al., *Magn. Reson. Chem.* 32, 705–710, (1994), to give a compound of formula XLI, which is a compound of formula I. Product formation occurs by initial addition of the primary amine to the imine followed by cyclization to the desired compound of formula XLI.

Scheme XXI

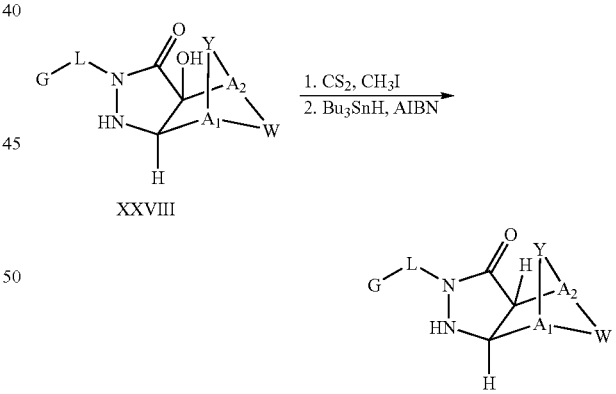

As illustrated in Scheme XXI, a compound of formula XXVIII can be readily deoxygenated by first treatment with carbon disulfide and methyl iodide to generate a xanthate ester intermediate. Then treatment with tributyltin hydride and AIBN, as described in Palomo, C. et al., *Tetrahedron Lett.* 33, 4827–4830, (1992), yields a compound of formula XLII, which is a compound of formula I.

Scheme XXII

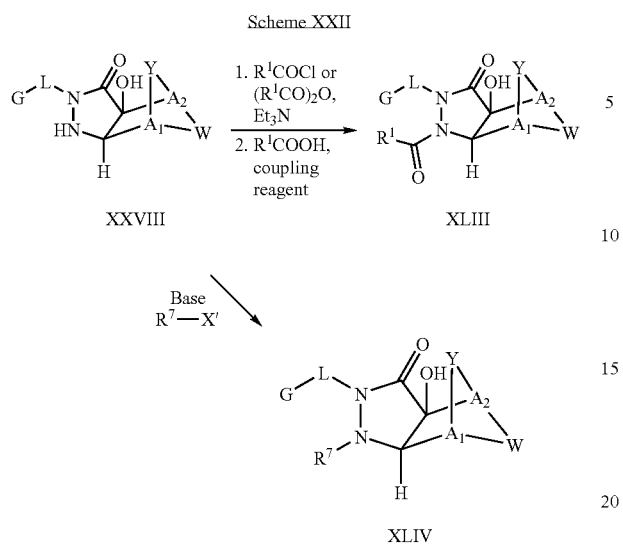

As illustrated in Scheme XXII, a compound of formula XXVIII can be converted to compounds of formula XLIII and XLIV, which are compounds of formula I. A compound of formula XXVIII can be treated with an acylating agent such as $R^1COCl$ or $(R^1CO)_2O$, with a base such as $Et_3N$, with or without heating, in a manner known to one skilled in the art, to generate a compound of formula XLIII. Alternatively, a compound of formula XVIII can be treated with an acid of formula $R^1COOH$ along with any of an array of peptide coupling reagents well known to one skilled in the art, to generate a compound of formula XLIII. A compound of formula XVIII can also be treated with a halide (e.g., alkyl halide) of formula $R^7$—X' ($R^7$ for this Scheme includes the groups defined for $R^4$, except (un)substituted aryl or heteroaryl), in the presence of a base such as $K_2CO_3$ or NaH, to yield an amine (e.g., alkyl amine) derivative of formula XLIV. Intermediates $R^1COCl$, $(R^1CO)_2O$ and $R^7$—X' can be obtained from commercial sources or prepared by one skilled in the art.

Other compounds of the invention can be made by procedures analogous to those above. For example, the above procedures can be employed wherein Z is S, NH or $NR^6$ in place of Z=oxygen as shown. Compounds of the formula I can also be made, wherever appropriate, by methods described in U.S. application Ser. No. 10/025,116 filed concurrently herewith by Mark Salvati et al., entitled "Fused Heterocyclic Succinimide Compounds and Analogs Thereof, Modulators of Nuclear Hormone Receptor Function, incorporated herein by reference it its entirety, such as by the microbial/enzymatic conversions and/or separation methods as described therein.

Preferred Compounds

A preferred subgenus of the compounds of the present invention includes compounds of the formula I or salts thereof wherein one or more, preferably all, of the substituents are as defined in formulae Ia to Id, and further, as defined below:

G is selected from optionally substituted phenyl, optionally substituted naphthyl and optionally substituted fused bicyclic heterocyclic groups such as optionally substituted benzo-fused heterocyclic groups (e.g., bonded to the remainder of the molecule through the benzene portion), especially such groups wherein the heterocyclic ring bonded to benzene has 5 members exemplified by benzoxazole, benzothiazole, benzothiadiazole, benzoxadiazole or benzothiophene, for example:

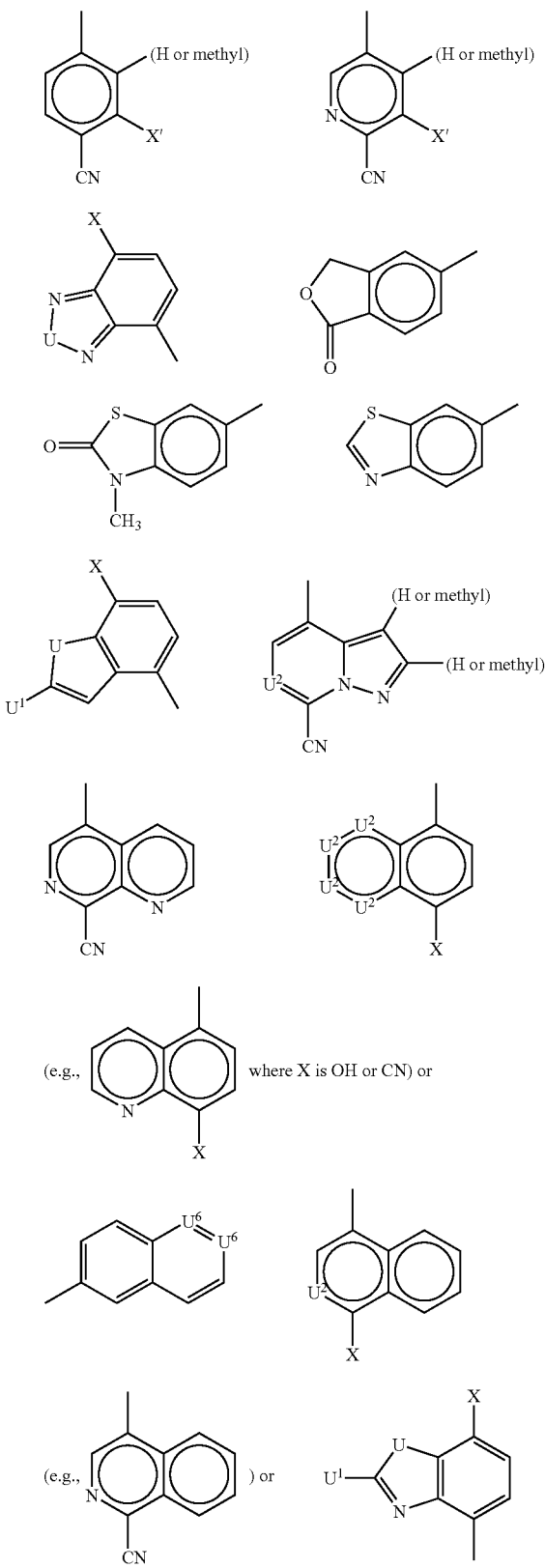

where
X=halo (especially F), OH, CN, NO$_2$ or

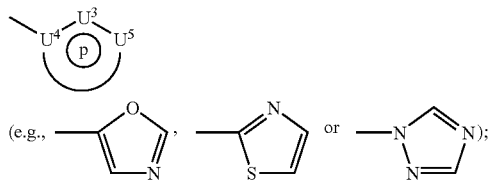

X'=halo (especially Cl, F, or I), CH$_3$, CF$_3$, CN or OCH$_3$;
U is O or S (where S can optionally be oxygenated, e.g., to SO);
U$^1$ is CH$_3$ or CF$_3$;
each U$^2$ is independently N, CH or CF;
U$^3$ is N, O or S;
U$^4$ and U$^5$, together with the atoms to which they are bonded, form an optionally substituted 5-membered heterocyclic ring which can be partially unsaturated or aromatic and which contains 1 to 3 ring heteroatoms;
each U$^6$ is independently CH or N; and

denotes optional double bond(s) within the ring formed by U$^3$, U$^4$ and U$^5$;
L is a bond;
Q$_1$ (and Q$_2$ when present) are independently H or OH;
A$_1$ and A$_2$ are independently CR$^7$ where R$^7$ is H, alkyl or substituted alkyl;
Y is O, CH$_2$ or CH$_2$—CH$_2$; and
W is CR$^8$=CR$^8$ or CR$^7$R$^{7\prime}$—CR$^7$CR$^{7\prime}$.

Use and Utility

The compounds of the present invention modulate the function of nuclear hormone receptors (NHR), and include compounds which are, for example, agonists, partial agonists, antagonists or partial antagonists of the androgen receptor (AR), the estrogen receptor (ER), the progesterone receptor (PR), the glucocorticoid receptor (GR), the mineralocorticoid receptor (MR), the steroid and xenobiotic receptor (SXR), other steroid binding NHR's, the Orphan receptors or other NHR's. Selective modulation of one such NHR relative to others within the NHR family is preferred. "Modulation" includes, for example, activation (e.g., agonist activity such as selective androgen receptor agonist activity) or inhibition (e.g., antagonist activity).

The present compounds are thus useful in the treatment of NHR-associated conditions. A "NHR-associated condition", as used herein, denotes a condition or disorder which can be treated by modulating the function of a NHR in a subject, wherein treatment comprises prevention (e.g., prophylactic treatment), partial alleviation or cure of the condition or disorder. Modulation may occur locally, for example, within certain tissues of the subject, or more extensively throughout a subject being treated for such a condition disorder.

The compounds of the present invention are useful for the treatment of a variety of conditions and disorders including, but not limited to, those described following:

Compounds of formula I can be applied as agonists, partial agonists, antagonists, or partial antagonists of the estrogen receptor, preferably selectively to that receptor, in an array of medical conditions which involve modulation of the estrogen receptor pathway. Applications of said compounds include but are not limited to: osteoporosis, hot flushes, vaginal dryness, prostate cancer, breast cancer, endometrial cancer, cancers expressing the estrogen receptor such as the aforementioned cancers and others, contraception, pregnancy termination, menopause, amennoreahea, and dysmennoreahea.

Compounds of formula I can be applied as agonists, partial agonists, antagonists or partial antagonists of the progesterone receptor, preferably selectively to that receptor, in an array of medical conditions which involve modulation of the progesterone receptor pathway. Applications of said compounds include but are not limited to: breast cancer, other cancers containing the progesterone receptor, endometriosis, cachexia, contraception, menopause, cyclesynchrony, meniginoma, dysmennoreahea, fibroids, pregnancy termination, labor induction and osteoporosis.

Compounds of formula I can be applied as agonists, partial agonists, antagonists or partial antagonists of the glucocorticoid receptor, preferably selectively to that receptor, in an array of medical conditions which involve modulation of the glucocorticoid receptor pathway. Applications of said compounds include but are not limited to: inflammatory diseases, autoimmune diseases, prostate cancer, breast cancer, Alzheimer's disease, psychotic disorders, drug dependence, non-insulin dependent Diabetes Mellitus, and as dopamine receptor blocking agents or otherwise as agents for the treatment of dopamine receptor mediated disorders.

Compounds of formula I can be applied as agonists, partial agonists, antagonists or partial antagonists of the mineralocorticoid receptor, preferably selectively to that receptor, in an array of medical conditions which involve modulation of the mineralocorticoid receptor pathway. Applications of said compounds include but are not limited to: drug withdrawal syndrome and inflammatory diseases.

Compounds of formula I can be applied as agonists, partial agonists, antagonists or partial antagonists of the aldosterone receptor, preferably selectively to that receptor, in an array of medical conditions which involve modulation of the aldosterone receptor pathway. One application of said compounds includes but is not limited to: congestive heart failure.

Compounds of formula I can be applied as agonists, partial agonists, antagonists or partial antagonists of the androgen receptor, preferably selectively to that receptor, in an array of medical conditions which involve modulation of the androgen receptor pathway. Applications of said compounds include but are not limited to: hirsutism, acne, seborrhea, Alzheimer's disease, androgenic alopecia, hypogonadism, hyperpilosity, benign prostate hypertrophia, adenomas and neoplasies of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers modulation of VCAM expression and applications therein for the treatment of heart disease, inflammation and immune modulations, modulation of VEGF expression and the applications therein for use as antiangiogenic agents, osteoporosis, suppressing spermatogenesis, libido, cachexia, endometriosis, polycystic ovary syndrome, anorexia, androgen supplement for age related decreased testosterone levels in men, male menopause, male hormone replacement, male and female sexual dysfunction, and inhibition of muscular atrophy in ambulatory patients. For example, pan AR modulation is contemplated, with prostate selective AR modulation ("SARM") being particularly preferred, such as for the treatment of early stage prostate cancers.

Compounds of formula I can be applied as (preferably, selective) antagonists of the mutated androgen receptor, for example, found in many tumor lines. Examples of such mutants are those found in representative prostate tumor cell lines such as LNCap, (T877A mutation, Biophys. Acta, 187, 1052 (1990)), PCa2b, (L701H & T877A mutations, J. Urol., 162, 2192 (1999)) and CWR22, (H874Y mutation, Mol. Endo., 11, 450 (1997)). Applications of said compounds include but are not limited to: adenomas and neoplasies of the prostate, breast cancer and endometrial cancer.

Compounds of formula I can be applied as agonists, partial agonists, antagonists or partial antagonists of the steroid and xenobiotic receptor, preferably selectively to that receptor, in an array of medical conditions which involve modulation of the steroid and xenobiotic receptor pathway. Applications of said compounds include but are not limited to: treatment of disregulation of cholesterol homeostasis, attenuation of metabolism of pharmaceutical agents by co-administration of an agent (compound of the present invention) which modulates the P450 regulator effects of SXR.

Along with the aforementioned NHR, there also exist a number of NHR for which the activating or deactivating ligands may not be characterized. These proteins are classified as NHR due to strong sequence homology to other NHR, and are known as the Orphan receptors. Because the Orphan receptors demonstrate strong sequence homology to other NHR, compounds of formula I include those which serve as modulators of the function of the Orphan NHR. Orphan receptors which are modulated by NHR modulators such as compounds within the scope of formula I are exemplified, but not limited to, those listed in Table 1. Exemplary therapeutic applications of modulators of said Orphan receptors are also listed in Table 1, but are not limited to the examples therein.

step of administering to a subject in need thereof at least one compound of formula I in an amount effective therefor. Other therapeutic agents such as those described below may be employed with the inventive compounds in the present methods (for example, separately, or formulated together as a fixed dose). In the methods of the present invention, such other therapeutic agent(s) can be administered prior to, simultaneously with or following the administration of the compound(s) of the present invention.

The present invention also provides pharmaceutical compositions comprising at least one of the compounds of the formula I capable of treating a NHR-associated condition in an amount effective therefor, and a pharmaceutically acceptable carrier (vehicle or diluent). The compositions of the present invention can contain other therapeutic agents as described below, and can be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

It should be noted that the compounds of the present invention are, without limitation as to their mechanism of action, useful in treating any of the conditions or disorders listed or described herein such as inflammatory diseases or cancers, or other proliferate diseases, and in compositions for treating such conditions or disorders. Such conditions and disorders include, without limitation, any of those described previously, as well as those described following such as: maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic malagia; treatment of acute fatigue syndrome and muscle loss following elective surgery (e.g., post-surgical rehabilitation); acceleration of wound healing; accelerating bone fracture

TABLE 1

Exemplary Orphan nuclear hormone receptors, form (M = monomeric, D = heterodimeric, H = homodimeric), tissue expression and target therapeutic applications. (CNS = central nervous system)

| Receptor | Form | Tissue Expression | Target Therapeutic Application |
| --- | --- | --- | --- |
| NURR1 | M/D | Dopaminergic Neurons | Parkinson's Disease |
| RZRβ | M | Brain (Pituitary), Muscle | Sleep Disorders |
| RORα | M | Cerebellum, Purkinje Cells | Arthritis, Cerebellar Ataxia |
| NOR-1 | M | Brain, Muscle, Heart, Adrenal, Thymus | CNS Disorders, Cancer |
| NGFI-Bβ | M/D | Brain | CNS Disorders |
| COUP-Tfα | H | Brain | CNS Disorders |
| COUP-TFβ | H | Brain | CNS Disorders |
| COUP-TFγ | H | Brain | CNS Disorders |
| Nur77 | H | Brain, Thymus, Adrenals | CNS Disorders |
| Rev-ErbAα | H | Muscle, Brain (Ubiquitous) | Obesity |
| HNF4α | H | Liver, Kidney, Intestine | Diabetes |
| SF-1 | M | Gonads, Pituitary | Metabolic Disorders |
| LXRα, β | D | Kidney (Ubiquitous) | Metabolic Disorders |
| GCNF | M/H | Testes, Ovary | Infertility |
| ERRα, β | M | Placenta, Bone | Infertility, Osteoporosis |
| FXR | D | Liver, Kidney | Metabolic Disorders |
| CARα | H | Liver, Kidney | Metabolic Disorders |
| PXR | H | Liver, Intestine | Metabolic Disorders |
| COUP-TF2 (ARP1) | D | Testis | Oncology/angiogenesis |
| RORbeta | M | CNS, retina, pineal gland | Metabolic Disorders |

The present invention thus provides methods for the treatment of NHR-associated conditions, comprising the repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; conteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength; and the conditions, diseases, and maladies collectively referenced to as "Syndrome X" or Metabolic Syndrome as detailed in Johannsson *J. Clin. Endocrinol. Metab.*, 82, 727–34 (1997).

The present compounds have therapeutic utility in the modulation of immune cell activation/proliferation, e.g., as competitive inhibitors of intercellular ligand/receptor binding reactions involving CAMs (Cellular Adhesion Molecules) and Leukointegrins. For example, the present compounds modulate LFA-ICAM 1, and are particularly useful as LFA-ICAM 1 antagonists, and in the treatment of all conditions associated with LFA-ICAM 1 such as immunological disorders. Preferred utilities for the present compounds include, but are not limited to: inflammatory conditions such as those resulting from a response of the nonspecific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The present compounds can be used in treating asthma or as an adjunct to minimize toxicity with cytokine therapy in the treatment of cancers. The present compounds can be employed in the treatment of all diseases currently treatable through steroid therapy. The present compounds may be employed for the treatment of these and other disorders alone or with other immunosuppressive or antiinflammatory agents. In accordance with the invention, a compound of the formula I can be administered prior to the onset of inflammation (so as to suppress an anticipated inflammation) or after the initiation of inflammation. When provided prophylactically, the immunosuppressive compound(s) are preferably provided in advance of any inflammatory response or symptom (for example, prior to, at, or shortly after the time of an organ or tissue transplant but in advance of any symptoms or organ rejection). The prophylactic administration of a compound of the formula I prevents or attenuates any subsequent inflammatory response (such as, for example, rejection of a transplanted organ or tissue, etc.) Administration of a compound of the formula I attenuates any actual inflammation (such as, for example, the rejection of a transplanted organ or tissue).

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremophor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 1 to 100 (for example, 15) mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

As mentioned above, the compounds of the present invention can be employed alone or in combination with each other and/or other suitable therapeutic agents useful in the treatment of NHR-associated conditions, e.g., an antibiotic or other pharmaceutically active material.

For example, the compounds of the present invention can be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention can also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with, growth hormone releasing factor and its analogs or growth hormone and its analogs or somatomedins including IGF-1 and IGF-2,or with alpha-adrenergic agonists, such as clonidine or serotinin $5-HT_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.,* 9, 1003–1008 (1999) and Hamann, L. G. et al., *J. Med. Chem.,* 42, 210–212 (1999).

A further use of the compounds of this invention is in combination with progesterone receptor agonists ("PRA"), such as levonorgestrel, medroxyprogesterone acetate (MPA).

The compounds of the present invention can be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the present invention include biguanides (e.g., metformin), glucosidase inhibitors (e.g,. acarbose), insulins (including insulin secretagogues or insulin sensitizers), meglitinides (e.g., repaglinide), sulfonylureas (e.g., glimepiride, glyburide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, steroidal or non-steroidal progesterone receptor agonists, RANK ligand antagonists, calcium sensing receptor antagonists, TRAP inhibitors, selective estrogen receptor modulators (SERM), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), WO 99/00353 (KaroBio) and GB98/284425 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®) integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, veraparmil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epothilones, cisplatin and carboplatin.

Compounds of the present invention can further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, and coenzyme Q-10.

In addition, compounds of the present invention can be used in combination with therapeutic agents used in the treatment of sexual dysfunction, including but not limited to PDE5 inhibitors, such as sildenafil or IC-351; with an antiresorptive agent, hormone replacement therapies, vitamin D analogues, calcitonins, elemental calcium and calcium supplements, cathepsin K inhibitors, MMP inhibitors, vitronectin receptor antagonists, Src $SH_2$ antagonists, vacular —$H^+$-ATPase inhibitors, progesterone receptor agonists, ipriflavone, fluoride, RANK antagonists, PTH and its analogues and fragments, Tibolone, HMG-CoA reductase inhibitors, SERM's, p38 inhibitors, prostanoids, 17-beta hydroxysteroid dehydrogenase inhibitors and Src kinase inhibitors.

Compounds of the present invention can be used in combination with male contraceptives, such as nonoxynol 9 or therapeutic agents for the treatment of hair loss, such as minoxidil and finasteride or chemotherapeutic agents, such as with LHRH agonists.

For their preferred anticancer or antiangiogenic use, the compounds of the present invention can be administered either alone or in combination with other anti-cancer and cytotoxic agents and treatments useful in the treatment of cancer or other proliferative diseases, for example, where the second drug has the same or different mechanism of action than the present compounds of formula I. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; EGFR inhibitors such as small molecule EGFR inhibitors, EGFR antibodies such as C225 (Erbitux); antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A–F and their analogs; plant-derived products, such as vinca alkaloids, epipodophyllotoxins, taxanes; and topiosomeraseinhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. Patent can be employed together with any NHR modulators (including, but not limited to, those of present invention) such as AR modulators, ER modulators, with LHRH modulators, or with surgical castration, especially in the treatment of cancer).

The combinations of the present invention can also be formulated or co-administered with other therapeutic agents that are selected for their particular usefulness in administering therapies associated with the aforementioned conditions. For example, the compounds of the invention may be formulated with agents to prevent nausea, hypersensitivity and gastric irritation, such as antiemetics, and $H_1$ and $H_2$ antihistaminics.

As it pertains to the treatment of cancer, the compounds of this invention are most preferably used alone or in combination with anti-cancer treatments such as radiation therapy and/or with cytostatic and/or cytotoxic agents, such as, but not limited to, DNA interactive agents, such as cisplatin or doxorubicin; inhibitors of farnesyl protein transferase, such as those described in U.S. Pat. No. 6,011,029; topoisomerase II inhibitors, such as etoposide; topoisomerase I inhibitors, such as CPT-11 or topotecan; tubulin stabilizing agents, such as paclitaxel, docetaxel, other taxanes, or epothilones; hormonal agents, such as tamoxifen; thymidilate synthase inhibitors, such as 5-fluorouracil; antimetabolites, such as methoxtrexate; antiangiogenic agents, such as angiostatin, ZD6474, ZD6126 and comberstatin A2; kinase inhibitors, such as her2 specific antibodies, Iressa and CDK inhibitors; histone deacetylase inhibitors, such as CI-994 and MS-27-275. Such compounds may also be combined with agents which suppress the production of circulating testosterone such as LHRH agonists or antagonists or with surgical castration. Exemplary combination therapies (e.g., for the treatment of prostate cancer) for use with a compound of the present invention include an LHRH modulator or prednisone.

The present invention also contemplates kits, for example, for the treatment of prostate cancer, comprising a first container (such as a vial) containing a pharmaceutical formulation comprising a compound of the present invention, said compound optionally in a pharmaceutically acceptable carrier, and a second container (such as a vial) containing a pharmaceutical formulation comprising one or more agents (such as an LHRH modulator) to be used in combination with said compound of the present invention, said agent(s) optionally in a pharmaceutically acceptable carrier.

For example, known therapies for advanced metastatic prostate cancer include "complete androgen ablation therapy" wherein tumor growth is inhibited by controlling the supply of androgen to the prostate tissues via chemical castration (castration serves to inhibit the production of circulating testosterone (T) and dihydrotestosterone (DHT)) followed by the administration of androgen receptor (AR) antagonists (which inhibit the function T/DHT derived from the conversion of circulating androgen precursors to T/DHT by the prostate tissue). The compounds of the present invention can be employed as AR antagonists in complete ablation therapy, alone or in combination with other AR antagonists such as Flutamide, Casodex, Nilutamide, or Cyproterone acetate.

The present invention provides compounds which can be used to treat patients suffering from prostate cancer resistant to androgen receptor antagonists which are not within formula I of the invention (or salts thereof), such as bicalutimide. The invention thus further contemplates a method of treating prostate cancer resistant to an androgen receptor antagonist other than those of formula I or salts thereof, comprising the step of administering to a patient in need thereof a compound capable of reducing the growth rate of the tumor mass of said cancer in an amount effective therefor. The term "reducing the growth rate of said tumor mass" denotes reduction in the growth rate (including, of course, stabilization or reduction in size) of said tumor mass upon treatment relative to the growth rate upon treatment with said androgen receptor antagonist other than those of formula I or salts thereof. Compounds of the formula I and pharmaceutically acceptable salts thereof of the present invention are preferred such compounds.

The present invention also contemplates use of an antiestrogen and/or aromatase inhibitor in combination with a compound of the present invention, for example, to assist in mitigating side effects associated with antiandrogen therapy such as gynecomastia. Exemplary antiestrogen and/or aromatase inhibitors include anastrozole (Arimidex), tamoxifen citrate (Nolvadex), exemestane (Aromasin), toremifene citrate (Fareston), letrozole (Femara), raloxifene hydrochloride (Evista), Faslodex, or 923 (Wyeth Ayerst).

The compounds of the present invention may be employed adjuvant to surgery.

Another application of the present compounds is in combination with antibody therapy such as but not limited to antibody therapy against PSCA. An additional application is in concert with vaccine/immune modulating agents for the treatment of cancer.

Compounds of the present invention can be employed in accordance with the methods described in U.S. Provisional Patent Application Ser. No. 60/284,438, entitled "Selective Androgen Receptor Modulators and Methods for Their Identification, Design and Use" filed Apr. 18, 2001 by Mark E. Salvati et al., which Provisional Patent Application is incorporated herein by reference in its entirety (including, but not limited to, reference to all specific compounds within formula I of the present invention), and U.S. patent application Ser. No. 09/885,827, entitled "Selective Androgen Receptor Modulators and Methods for Their Identification, Design and Use" filed Jun. 20, 2001 by Mark E. Salvati et al., which Patent Application is incorporated herein by reference in its entirety (including, but not limited to, reference to all specific compounds within formula I of the present invention).

For racemates of compounds of the present invention, one enantiomer can, for example be a full AR antagonist while the other can be an AR antagonist in tumor tissue while having no activity or agonist activity in nontumor tissue containing the androgen receptor.

The above other therapeutic agents, when employed in combination with the compounds of the present invention, can be used, for example, in those amounts indicated in the Physicians' Desk Reference (PDR) or as otherwise determined by one of ordinary skill in the art.

The following assays can be employed in ascertaining the activity of a compound as a NHR modulator. Preferred are those compounds with an activity greater than 20 μm for binding or transactivation in any of these assays. Various compounds of the present invention were determined to have AR modulator activity utilizing the transactivation assay, and standard AR binding assays as described following.

Transactivation Assays:

AR Specific Assay:

Compounds of the present invention were tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., *J. Steroid Biochem. Molec. Biol.* 773 (1992), the disclosure of which is herein incorporated by reference.

For the transactivation assay a reporter plasmid is introduced by transfection (a procedure to induce cells to take foreign genes) into the respective cells. This reporter plasmid, comprising the cDNA for a reporter protein, such as secreted alkaline phosphatase (SEAP), controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and MDA 453 cells were obtained from the American Type Culture Collection (Rockville, Md.), and maintained in RPMI 1640 or DMEM medium supplemented with 10% fetal bovine serum (FBS; Gibco) respectively. The respective cells were transiently transfected by electroporation according to the optimized procedure described by Heiser, 130 Methods Mol. Biol., 117 (2000), with the pSEAP2/PSA540/Enhancer reporter plasmid. The reporter plasmid, was constructed as follows: commercial human placental genomic DNA was used to generate by Polymerase Cycle Reaction (PCR) a fragment containing the BglII site (position 5284) and the Hind III site at position 5831 of the human prostate specific antigen promoter (Accession #U37672), Schuur, et al., *J. Biol. Chem.*, 271 (12): 7043–51 (1996). This fragment was subcloned into the pSEAP2/basic (Clontech) previously digested with BglII and HindIII to generate the pSEAP2/PSA540 construct. Then a fragment bearing the fragment of human PSA upstream sequence between positions –5322 and –3873 was amplified by PCR from human placental genomic DNA. A XhoI and a BglII sites were introduced with the primers. The resulting fragment was subcloned into pSEAP2/PSA540 digested with XhoI and BglII respectively, to generate the pSEAP2/PSA540/Enhancer construct. LNCaP and MDA 453 cells were collected in media containing 10% charcoal stripped FBS. Each cell suspension was distributed into two Gene Pulser Cuvetts (Bio-Rad) which then received 8 μg of the reporter construct, and electoporated using a Bio-Rad Gene Pulser at 210 volts and 960 μFaraday. Following the transfections the cells were washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from 10-10 to 10-5 M (sample). Duplicates were used for each sample. The compound dilutions were performed on a Biomek 2000 laboratory workstation. After 48 hours, a fraction of the supernatant was assayed for SEAP activity using the Phospha-Light Chemiluminescent Reporter Gene Assay System (Tropix, Inc). Viability of the remaining cells was determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading was normalized by the Abs490 value derived from the MTS assay. For the antagonist mode, the % Inhibition was calculated as:

% Inhibition=100×(1−[average control−average blank/average sample−average blank])

Data was plotted and the concentration of compound that inhibited 50% of the normalized SEAP was quantified ($IC_{50}$).

For the agonist mode % Control was referred as the effect of the tested compound compared to the maximal effect observed with the natural hormone, in this case DHT, and was calculated as:

% Control=100×average sample−average blank/average control−average blank

Data was plotted and the concentration of compound that activates to levels 50% of the normalized SEAP for the control was quantified ($EC_{50}$).

GR Specificity Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR see, e.g. G. Chalepakis et al., Cell, 53(3), 371 (1988). This plasmid was transfected into A549 cells, which expresses endogenous GR, to obtain a GR specific transactivation assay. A549 cells were obtained from the American Type Culture Collection (Rockville, Md.), and maintained in RPMI 1640 supplemented with 10% fetal bovine serum (FBS; Gibco). Determination of the GR specific antagonist activity of the compounds of the present invention was identical to that described for the AR specific transactivation assay, except that the DHT was replaced with 5 nM dexamethasone (Sigma Chemicals), a specific agonist for GR. Determination of the GR specific agonist activity of the compounds of the present invention was performed as described for the AR transactivation assay, wherein one measures the activation of the GR specific reporter system by the addition of a test compound, in the absence of a known GR specific agonists ligand.

PR Specific Assay:

The reporter plasimid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR. This plasmid was transfected into T47D, which expresses endogenous PR, to obtain a PR specific transactivation assay. T47D cells were obtained from the American Type Culture Collection (Rockville, Md.), and maintained in DMEM medium supplemented with 10% fetal bovine serum (FBS; Gibco). Determination of the PR specific antagonist activity of the compounds of the present invention was identical to that described for the AR specific transactivation assay, except that the DHT was replaced with 1 nM Promegastone (NEN), a specific agonist for PR. Determination of the PR specific agonist activity of the compounds of the present invention was performed as described for the AR transactivation assay, wherein one measures the activation of the PR specific reporter system by the addition of a test compound, in the absence of a known PR specific agonists ligand.

AR Binding Assay:

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, were incubated at 37° C. to remove any endogenous ligand that might be complexed with the receptor in the cells. After 48 hours, either a saturation analysis to determine the $K_d$ for tritiated dihydrotestosterone, [$^3$H]-DHT, or a competitive binding assay to evaluate the ability of test compounds to compete with [$^3$H]-DHT were performed. For the saturation analysis, media (RPMI 1640 or DMEM–0.2% CA-FBS) containing [$^3$H]-DHT (in concentrations ranging from 0.1 nM to 16 nM) in the absence (total binding) or presence (non-specific binding) of a 500-fold molar excess of unlabeled DHT were added to the cells. After 4 hours at 37° C., an aliquot of the total binding media at each concentration of [$^3$H]-DHT was removed to estimate the amount of free [$^3$H]-DHT. The remaining media was removed, cells were washed three times with PBS and harvested onto UniFilter GF/B plates (Packard), Microscint (Packard) was added and plates counted in a Top-Counter (Packard) to evaluate the amount of bound [$^3$H]-DHT.

For the saturation analysis, the difference between the total binding and the non-specific binding, was defined as specific binding. The specific binding was evaluated by Scatchard analysis to determine the $K_d$ for [$^3$H]-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45–99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M were added to the cells. Two replicates were used for each sample. After 4 hours at 37° C., cells were washed, harvested and counted as described above. The data was plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand was quantified (IC$_{50}$) after log-logit transformation. The $K_I$ values were determined by application of the Cheng-Prusoff equation to the IC$_{50}$ values, where:

$$K_I = \frac{IC_{50}}{\left(1 + ([^3\text{H-DHT}])/K_d \text{ for }^3\text{H-DHT}\right)}.$$

After correcting for non-specific binding, IC$_{50}$ values were determined. The IC$_{50}$ is defined as the concentration of competing ligand needed to reduce specific binding by 50%. The $K_d$s for [$^3$H]-DHT for MDA 453 and LNCaP were 0.7 and 0.2 nM respectively.

Human Prostate Cell Proliferation Assay:

Compounds of the present invention were tested ("test compounds") on the proliferation of human prostate cancer cell lines. For that, MDA PCa2b cells, a cell line derived from the metastasis of a patient that failed castration, Navone et al., *Clin. Cancer Res.*, 3, 2493–500 (1997), were incubated with or without the test compounds for 72 hours and the amount of [$^3$H]-thymidine incorporated into DNA was quantified as a way to assess number of cells and therefore proliferation. The MDA PCa2b cell line was maintained in BRFF-HPC1 media (Biological Research Faculty & Facility Inc., MD) supplemented with 10% FBS. For the assay, cells were plated in Biocoated 96-well microplates and incubated at 37° C. in 10% FBS (charcoal-stripped)/BRFF-BMZERO (without androgens). After 24 hours, the cells were treated in the absence (blank) or presence of 1 nM DHT (control) or with test compounds (sample) of the present invention in concentrations ranging from $10^{-10}$ to $10^{-5}$ M. Duplicates were used for each sample. The compound dilutions were performed on a Biomek 2000 laboratory work station. Seventy two hours later 0.44 uCi. of [$^3$H]-Thymidine (Amersham) was added per well and incubated for another 24 h followed by tripsinization, harvesting of the cells onto GF/B filters. Micro-scint PS were added to the filters before counting them on a Beckman TopCount.

The % Inhibition was calculated as:

% Inhibition=100×(1−[average$_{control}$−average$_{blank}$/average$_{sample}$−average$_{blank}$])

Data was plotted and the concentration of compound that inhibited 50% of the [$^3$H]-Thymidine incorporation was quantified (IC$_{50}$).

C2C12 Mouse Myoblast Transactivation Assay:

Two functional transactivation assays were developed to assess the efficacy of androgen agonists in a muscle cell background using a luciferase reporter. The first assay (ARTA Stable 1) uses a cell line, Stable 1 (clone #72), which stably expresses the full length rat androgen receptor but requires the transient transfection of an enhancer/reporter. This cell line was derived from C2C12 mouse moyoblast cells. The second assay (ARTA Stable 2) uses a cell line, Stable 2 (clone #133), derived from Stable 1 which stably expresses both rAR and the enhancer/luciferase reporter.

The enhancer/reporter construct used in this system is pGL3/2XDR-1/luciferase. 2XDR-1 was reported to be an AR specific response element in CV-1 cells, Brown et. al. *The Journal of Biological Chemistry* 272, 8227–8235, (1997). It was developed by random mutagenesis of an AR/GR consensus enhancer sequence.

ARTA Stable 1:
1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.:

SH30068.02), 50 mM HEPES Buffer (Gibco BRL, Cat. No.: 15630-080), 1×MEM Na Pyruvate (Gibco BRL, Cat. No.: 11360–070), 0.5×Antibiotic-Antimycotic, and 800 µg/ml Geneticin (Gibco BRL, Cat. No.: 10131-035).

2. 48 hours later, cells are transfected with pGL3/2XDR-1/ luciferase using LipofectAMINE Plus™ Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 µl/well Opti-MEMem media (Gibco BRL, Cat. No.: 31985-070). To this, 0.5 µl/well Plus reagent is added. This mixture is incubated for 15 minutes at room temperature. In a separate vessel, 0.385 µl/well LipofectAMINE reagent is diluted with 5 µl/well Opti-MEM. The DNA mixture is then combined with the LipofectAMINE mixture and incubated for an additional 15 minutes at room temperature. During this time, the media from the cells is removed and replaced with 60 µl/well of Opti-MEM. To this is added 10 µl/well of the DNA/LipofectAMINE transfection mixture. The cells are incubated for 4 hours.

3. The transfection mixture is removed from the cells and replaced with 90 µl of media as in #1 above.

4. 10 µl/well of appropriate drug dilution is placed in each well.

5. 24 hours later, the Steady-Glo™ Luciferase Assay System is used to detect activity according to the manufacturer's instructions (Promega, Cat. No.: E2520).

ARTA Stable 2

1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5×Antibiotic-Antimycotic, 800 µg/ml Geneticin (Gibco BRL, Cat. No.: 10131-035) and 800 µg/ml Hygromycin β (Gibco BRL, Cat. No.: 10687-010).

2. 48 hours later, the media on the cells is removed and replaced with 90 µl fresh. 10 µl/well of appropriate drug dilution is placed in each well.

3. 24 hours later, the Steady-Glo™ Luciferase Assay System is used to detect activity according to the manufacturer's instructions (Promega, Cat. No.: E2520).

See U.S. patent application Ser. No. 09/885,831, entitled "Cell Lines and Cell-Based Assays for Identification of Androgen Receptor Modulators" filed Jun. 20, 2001 by Jacek Ostrowski et al, which Patent Application is incorporated herein by reference in its entirety.

Proliferation Assays

Murine Breast Cell Proliferation Assay:

The ability of compounds of the present invention ("test compounds") to modulate the function of the AR was determined by testing said compounds in a proliferation assay using the androgen responsive murine breast cell line derived from the Shionogi tumor, Hiraoka et al., *Cancer Res.*, 47, 6560–6564 (1987). Stable AR dependent clones of the parental Shionogi line were established by passing tumor fragments under the general procedures originally described in Tetuo, et. al., *Cancer Research* 25, 1168–1175 (1965). From the above procedure, one stable line, SC114, was isolated, characterized and utilized for the testing of example compounds. SC114 cells were incubated with or without the test compounds for 72 hours and the amount of [3H]-thymidine incorporated into DNA was quantified as a surrogate endpoint to assess the number of cells and therefore the proliferation rate as described in Suzuki et. al., *J. Steroid Biochem. Mol. Biol.* 37, 559–567 (1990). The SC114 cell line was maintained in MEM containing $10^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1:1, v/v) containing 0.1% BSA] with (antagonist mode) or without (agonist mode) $10^{-8}$ M testosterone and the test compounds of the present invention in concentrations ranging from $10^{-10}$ to $10^{-5}$ M. Duplicates were used for each sample. The compound dilutions were performed on a Biomek 2000 laboratory work station. Seventy two hours later 0.44 uCi of [3H]-Thymidine (Amersham) was added per well and incubated for another 2 hr followed by tripsinization, and harvesting of the cells onto GF/B filters. Micro-scint PS were added to the filters before counting them on a Beckman TopCount.

For the antagonist mode, the % Inhibition was calculated as:

$$\% \text{ Inhibition} = 100 \times (1 - [\text{average}_{sample} - \text{average}_{blank} / \text{average}_{control} - \text{average}_{blank}])$$

Data was plotted and the concentration of compound that inhibited 50% of the [3H]-Thymidine incorporation was quantified ($IC_{50}$).

For the agonist mode % Control was referred as the effect of the tested compound compared to the maximal effect observed with the natural hormone, in this case DHT, and was calculated as:

$$\% \text{ Control} = 100 \times (\text{average}_{sample} - \text{average}_{blank}) / (\text{average}_{control} - \text{average}_{blank})$$

Data was plotted and the concentration of compound that inhibited 50% of the [3H]-Thymidine incorporation was quantified ($EC_{50}$).

In Vitro Assay to Measure GR Induced AP-1 Transrepression:

The AP-1 assay is a cell based luciferase reporter assay. A549 cells, which contain endogenous glucocorticoid receptor, were stably transfected with an AP-1 DNA binding site attached to the luciferase gene. Cells are then grown in RPMI+10% fetal calf serum (charcoal-treated)+Penicillin/Streptomycin with 0.5 mg/ml geneticin. Cells are plated the day before the assay at approximately 40000 cells/well. On assay day, the media is removed by aspiration and 20 µl assay buffer (RPMI without phenol red+10% FCS (charcoal-treated)+Pen/Strep) is added to each well. At this point either 20 µl assay buffer (control experiments), the compounds of the present invention ("test compounds") (dissolved in DMSO and added at varying concentrations) or dexamethasome (100 nM in DMSO, positive control) are added to each well. The plates are then pre-incubated for 15 minutes at 37° C., followed by stimulation of the cells with 10 ng/ml PMA. The plates are then incubated for 7 hrs at 37° C. after which 40 µl luciferase substrate reagent is added to each well. Activity is measured by analysis in a luminometer as compared to control experiments treated with buffer or dexamethasome. Activity is designated as % inhibition of the reporter system as compared to the buffer control with 10 ng/ml PMA alone. The control, dexamethasone, at a concentration of $\leq 10$ µM typically suppresses activity by 65%. Test compounds which demonstrate an inhibition of PMA induction of 50% or greater at a concentration of test compound of $\leq 10$ µM are deemed active.

Wet Prostate Weight Assay AR Antagonist Assay:

The activity of compounds of the present invention as AR antagonists was investigated in an immature male rat model, a standard, recognized test of antiandrogen activity of a given compound, as described in L. G. Hershberger et al., Proc. Soc. Expt. Biol. Med., 83, 175 (1953); P. C. Walsh and R. F. Gittes, "Inhibition of extratesticular stimuli to prostate growth in the castrated rat by antiandrogens", Endocrinology, 86, 624 (1970); and B. J. Furr et al., "ICI 176,334: A novel non-steroid, peripherally selective antiandrogen", J. Endocrinol., 113, R7–9 (1987), the disclosures of which are herein incorporated by reference.

The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al. Clin. Invest. Med., 16, 475–492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, "The Physiology of Reproduction" ed. By E. Knobil and J. D. Neill, 1, 1435–1487 (1994). Since the male sex organs are the tissues most responsive to modulation of the androgen activity, this model is used to determine the androgen dependent growth of the sex accessory organs in immature castrated rats.

Male immature rats (19–20 days old Sprague-Dawley, Harlan Sprague-Dawely) were castrated under metofane ansestesia. Five days after surgery these castrated rats (60–70 g, 23–25 day-old) were dosed for 3 days. Animals were dosed sub-cutaneously (s.c.) 1 mg/kg with Testosterone Proprionate (TP) in arachis oil vehicle and antiandrogen test compounds (compounds of the present invention) were dosed orally by gavage (p.o.) in dissolved/suspensions of 80% PEG 400 and 20% Tween 80 (PEGTW). Animals were dosed (v/w) at 0.5 ml of vehicle/100 g body weight. Experimental groups were as follows:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 3-day treatment, the animals were sacrificed, and the ventral prostate weighed. To compare data from different experiments, the sexual organs weights were first standardized as mg per 100 g of body weight, and the increase in organ weight induced by TP was considered as the maximum increase (100%). ANOVA followed by one-tailed Student or Fischer's exact test was used for statistical analysis.

The gain and loss of sexual organ weight reflect the changes of the cell number (DNA content) and cell mass (protein content), depending upon the serum androgen concentration. See Y. Okuda et al., J. Urol., 145, 188–191 (1991), the disclosure of which is herein incorporated by reference. Therefore, measurement of organ wet weight is sufficient to indicate the bioactivity of androgens and androgen antagonist. In immature castrated rats, replacement of exogenous androgens increases seminal vesicles (SV) and the ventral prostate (VP) in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10–30-fold higher potency than free T.

In this immature castrated rat model, a known AR antagonist (Casodex) was also administered simultaneously with 0.1 mg of TP ($ED_{80}$), inhibiting the testosterone-mediated increase in the weights of the VP and SV in a dose dependent manner. The antagonist effects were similar when dosing orally or subcutaneously. Compounds of the invention also exhibited AR antagonist activity by suppressing the testosterone-mediated increase in the weights of VP and SV. Levator Ani & Wet Prostate Weight Assay AR Agonist Assay:

The activity of compounds of the present invention as AR agonists was investigated in an immature male rat model, a recognized test of anabolic effects in muscle and sustaining effects in sex organs for a given compound, as described in L. G. Hershberger et al., Proc. Soc. Expt. Biol. Med., 83, 175 (1953); B. L. Beyler et al, "Methods for evaluating anabolic and catabolic agents in laboratory animals", J. Amer. Med. Women's Ass., 23, 708 (1968); H. Fukuda et al., "Investigations of the levator ani muscle as an anabolic steroid assay", Nago Dai. Yak. Ken. Nem. 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized. M. Masuoka et al., "Constant cell population in normal, testosterone deprived and testosterone stimulated levator ani muscles" Am. J. Anat. 119, 263 (1966); Z. Gori et al., "Testosterone hypertrophy of levator ani muscle of castrated rats. I. Quantitative data" Boll.—Soc. Ital. Biol. Sper. 42, 1596 (1966); Z. Gori et al., "Testosterone hypertrophy of levator ani muscle of castrated rats. II. Electron-microscopic observations" Boll.—Soc. Ital. Biol. Sper. 42, 1600 (1966); A. Boris et al., Steroids 15, 61 (1970). As described above, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200–250 g, 6–8 weeks-old, Sprague-Dawley, Harlan) were acquired castrated from the vendor (Taconic). The rats were divided into groups and treated daily for 7 to 14 days with one of the following:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 7–14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Super-anova (one factor) was used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188–191 (1991), the disclosure of which is herein incorporated by reference. Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10–30-fold higher potency than free T.

MDA PCa2b Human Prostate Zenograft Assay:

In Vivo Antitumor Testing: MDA-PCa-2b human prostate tumors were maintained in Balb/c nu/nu nude mice. Tumors were propagated as subcutaneous transplants in adult male nude mice (4–6 weeks old) using tumor fragments obtained from donor mice. Tumor passage occurred every 5–6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approx. 100–200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight= (length×width2)÷2

Tumor response end-point was expressed in terms of tumor growth inhibition (% T/C), defined as the ratio of median tumor weights of the treated tumors (T) to that of the control group (C).

To estimate tumor cell kill, the tumor volume doubling time was first calculated with the formula:

TVDT=Median time (days) for control tumors to reach target size−Median time (days) for control tumors to reach half the target size s And, Log cell kill=(T−C)÷(3.32×TVDT)

Statistical evaluations of data were performed using Gehan's generalized Wilcoxon test.

Dunning Prostate Tumor:

Dunning R3327H prostate tumor is a spontaneously derived, well differentiated androgen responsive adenocarcinoma of the prostate (Smolev J K, Heston W D, Scott W W, and Coffey D S, *Cancer Treat Rep.* 61, 273–287 (1977)). The growth of the R3327H subline has been selected for its highly androgen-dependent and reproducible growth in intact male rats. Therefore, this model and other sublines of this tumor have been widely used to evaluate in vivo antitumor activities of antiandrogens such as flutamide and bacilutamide/Casodex (Maucher A., and von Angerer, *J. Cancer Res. Clin. Oncol.*, 119, 669–674 (1993), Furr B. J. A. *Euro. URL.* 18 (suppl. 3), 2–9 (1990), Shain S. A. and Huot RI. *J. Steriod Biochem.* 31, 711–718 (1988)).

At the beginning of the study, the Dunning tumor pieces (about 4×4 mm) are transplanted subcutaneously to the flank of mature male Copenhagen rats (6–7 weeks old, Harlan-Sprague Dawley, Indianapolis, Md.). About 6 weeks after the implantation, the animals with tumors of measurable size (about 80–120 $mm^2$) are randomized into treatment groups (8–10 rats/group) and the treatments are initiated. One group of the rats are castrated to serve as the negative control of tumor growth. Animals are treated daily with compounds of the current invention, standard antiandrogens such as bacilutamide or vehicle (control) for an average of 10 to 14 weeks. Test compounds are dissolved in a vehicle of (2.5 ml/kg of body weight) 10% polyethylene glycol and 0.05% Tween-80 in 1% carboxymethyl cellulose, PEG/CMC, (Sigma, St Louis, Mo.). Typical therapeutic experiments would include three groups of three escalating doses for each standard or test compound (in a range of 300–3 mg/kg).

Tumors in the vehicle (control) group reach a size of 1500 to 2500 $mm^3$, whereas the castrated animal group typically shows tumor stasis over the 14 weeks of observation. Animals treated orally with 20 mg/kg of bicalutamide or flutamide would be expected to show a 40% reduction in tumor volumes compared to control after 14 weeks of treatment. The size of tumors are measured weekly by vernier caliper (Froboz, Switzerland), taking perpendicular measurements of length and width. Tumor volumes are measured in $mm^3$ using the formula: Length×Width×Height=Volume. Statistical differences between treatment groups and control are evaluated using multiple ANOVA analysis followed by one tail non-parametric Student t test.

Mature Rat Prostate Weight Assay:

The activity of compounds of the present invention were investigated in a mature male rat model, which is a variation of the Levator ani & wet prostate weight assay described above. The above in vivo assays are recognized assays for determining the anabolic effects in muscle and sustaining effects in sex organs for a given compound, as described in L. G. Hershberger et al., 83 *Proc. Soc. Expt. Biol. Med.,* 175 (1953); B. L. Beyler et al, "Methods for evaluating anabolic and catabolic agents in laboratory animals", 23 *J. Amer. Med. Women's Ass.,* 708 (1968); H. Fukuda et al., "Investigations of the levator ani muscle as an anabolic steroid assay", 14 *Nago Dai. Yak. Ken. Nem.* 84 (1966) the disclosures of which are herein incorporated by reference. The basis of this assay lies in the well-defined action of androgenic agents on the maintenance and growth of muscle tissues and sexual accessory organs in animals and man.

The male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie. et. al. 16 *Clin. Invest. Med.,* 475–492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues, M. C. Luke and D. S. Coffey, "The Physiology of Reproduction" ed. By E. Knobil and J. D. Neill, 1, 1435–1487 (1994). Since the male sex organs and the levator ani are the tissues most responsive to modulation of the androgen activity, this model is used to determine the activity of compounds that modulate the androgen receptor pathway in mature rats.

Along with its mitogenic activity on tissues such as prostate, seminal vesicle and muscle, testosterone also serves as a negative regulator for its own biosynthesis. Testosterone production in the Leydig cells of the testis is controlled by the level of circulating LH released from the pituitary gland. LH levels are themselves controlled by the level of LHRH produced in the hypothalmic region. Testosterone levels in the blood serve to inhibit the secretion of LHRH and subsequently reduce levels of LH and ultimately the levels of circulating testosterone levels. By measuring blood levels of LH as they are-effected by compounds of the present invention ("test compounds"), it is possible to determine the level of agonist or antagonist activity of said compounds at the hypothalamic axis of this endocrine cycle.

Matched sets of Harlan Sprague-Dawely rats (40–42 days old, 180–220 g), were dosed orally by gavage (p.o.) with the test compounds in dissolved/suspensions of 80% PEG 400 and 20% Tween 20 (PEGTW) for 14 days. Two control groups, one intact and one castrated were dose orally only with the PEGTW vehicle. Animals were dosed (v/w) at 0.5 ml of vehicle /100 g body weight. Experimental groups were as follows:
1. Intact vehicle (p.o., PEGTW, QD)
2. Control vehicle (p.o., PEGTW, QD)
3. Bicalutamide (Casodex, a recognized antiandrogen, as a reference compound) or a compound of the present invention, p.o. in PEGTW QD. (in a range of doses).

At the end of the 14-day treatment, the animals were sacrificed, and the ventral prostate, the seminal vesicles, and the levator ani were removed surgically and weighed. To compare data from different experiments, the organs weights were first standardized as mg per 100 g of body weight, and expressed as a percentage of the value of the respective organ in the intact group.

Rat luteinizing hormone (rLH) is quantitatively determined with the Biotrak [125 I] kit (Amersham Pharmacia Biotek), following the manufacturer directions. The assay is based on the competition by the LH present in the serum of the binding of [$^{125}$I] rLH to an Amerlex-M bead/antibody suspension. The radioactivity that remains after incubation with the serum and subsequent washes is extrapolated into a standard curve to obtain a reading in ng/ml.

The gain and loss of sexual organ and levator ani weight reflect the changes of the cell number (DNA content) and cell mass (protein content), depending upon the serum androgen concentration, see Y. Okuda et al., *J. Urol.,* 145, 188–191 (1991), the disclosure of which in herein incorporated by reference. Therefore, measurement of organ wet weight is sufficient to indicate the bioactivity of androgens and androgen antagonist. In the mature rats assay, active agonist agents will have no effect or will increase the weight of one or more of the androgen responsive organs (levator ani, prostate, seminal vessicle) and will have no effect or a suppressive effect on LH secretion. Compounds with antagonist activity will decrease the weight of one or more of the androgen responsive organs (levator ani, prostate, seminal vesicle) and will have no effect or a reduced suppressive effect on LH secretion.

CWR22 Human Prostate Zenograft Assay:

In Vivo Antitumor Testing: CWR22 human prostate tumors were maintained in Balb/c nu/nu nude mice. Tumors were propagated as subcutaneous transplants in adult male nude mice (4–6 weeks old) using tumor fragments obtained from donor mice. Tumor passage occurred every 5–6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approx. 100–200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight= (length×width2)÷2.

Tumor response end-point was expressed in terms of tumor growth inhibition (% T/C), defined as the ratio of median tumor weights of the treated tumors (T) to that of the control group (C).

To estimate tumor cell kill, the tumor volume doubling time was first calculated with the formula:

TVDT=Median time (days) for control tumors to reach target size−Median time (days) for control tumors to reach half the target size And, Log cell kill=(T−C)÷(3.32×TVDT)

Statistical evaluations of data were performed using Gehan's generalized Wilcoxon test.

The following Examples illustrate embodiments of the present invention, and are not intended to limit the scope of the claims.

ABBREVIATIONS

The following abbreviations are used herein:
DBU=1,8-diazabicyclo[5.4.0]undec-7-ene
4-DMAP=4-dimethylaminopyridine
ee=enantiomeric excess
DMF=dimethylformamide
EtOAc=ethyl acetate
LDA=lithium diisopropylarmide
Hünig's Base=N,N-diisopropylethylamine
Me=methyl
RT=retention time
TFA=trifluoroacetic acid
THF=tetrahydrofuran
TLC=thin layer chromatography
TMS=trimethylsilyl
pTSA=para-toluenesulfonic acid
Δ=heat
t-Bu=tert-butyl
PhCH$_3$=toluene
Pd/C=palladium on activated charcoal
TsCl=tosyl chloride
TBSOTf=tert-butyldimethylsilyl trifluoromethane sulfonate
TBS=tert-butyldimethylsilane
MeI=methyl iodide
(BOC)$_2$O=di-tert-butyl dicarbonate
TEA=triethylamine
n-BuLi=n-butyllithium
rt=room temperature
LC=liquid chromatography
Ts=tosyl
Ph=phenyl
EtOH=ethanol
DCE=dichloroethane
DMSO=dimethylsulfoxide
Ra-Ni=Raney Nickel
MS=molecular sieves
MS(ES)=Electro-Spray Mass Spectrometry
mCPBA=m-chloroperoxybenzoic acid
sat=saturated
AcOH=acetic acid
MeOH=methanol
Et$_2$O=diethyl ether
Ac=acetyl
DEAD=diethyl azodicarboxylate
h=hours
Et=ethyl
WSDCC=water soluble dicarbonyl diimide, 1-(3-dimethylaminopropyl)-3-ethylcarbodiimide hydrochloride
TBAF=tetrabutylammonium fluoride
DBAD=di-terbutylazodicarboxylate
DCC=Dicyclohexylcarbodiimide
Wilkinson's catalyst=RhCl(PPh$_3$)$_3$
ADDP=1,1-[azodicarbonyl]dipiperidine
DMA=dimethylacetamide
DME=1,2-dimethoxyethane
BOP=benzotriazol-1-yloxytris(dimethylanino)-phosphonium
Hexafluorophosphate

EXAMPLE 1

(3aα,4α,7α,7aα)-2-(3-Chloro-4-fluorophenyl)-3a,4,7,7a-tetrahydro-4,7-methano-1,2-benzisothiazol-3(2H)-one-1,1-dioxide (1B)

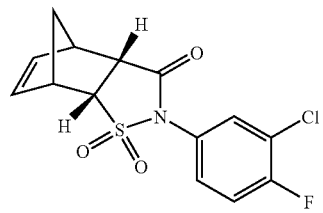

A. 2-(3-Chloro-4-fluoro-phenyl)-1,1-dioxo-1,2-dihydro-1λ$^6$-isothiazol-3-one (1A)

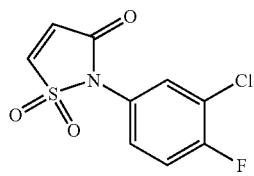

To a solution of 2-(3-chloro-4-fluoro-phenyl)-isothiazol-3-one (0.399 g, 1.74 mmol, obtained commercially) in methylene chloride (30 mL) at 0° C. was added mCPBA (60% mixture, 1.50 g, 5.21 mmol). The reaction was then warmed to 25° C. After 2 h, sat. aq. NaHCO$_3$ (25 mL) was added with vigorous stirring. After 0.5 h, the mixture was extracted with methylene chloride (3×30 mL) and the combined organics were dried over anhydrous sodium sulfate and concentrated in vacuo. The crude material was purified by flash chromatography on silica eluting with methylene chloride to give 0.296 g of compound 1A as a white powder. HPLC: 97% at 3.217 min (retention time) (YMC S5 ODS column 4.6×50 mm eluting with 10–90% aqueous methanol over 4 minutes containing 0.2% phosphoric acid, 4 mL/min, monitoring at 220 nm).

B. (3aα,4α,7α,7aα)-2-(3-Chloro-4-fluorophenyl)-3a,4,7,7a-tetrahydro-4,7-methano-1,2-benzisothiazol-3(2H)-one, 1,1-dioxide (1B)

To a solution of compound 1A (0.050 g, 0.192 mmol) in methylene chloride (3.0 mL) at 0° C. was added freshly cracked cyclopentadiene (0.025 g, 0.383 mmol). The reaction was then warmed to 25° C. After 20 min, the reaction was concentrated in vacuo and then purified by preparative TLC on silica eluting with 3% EtOAc in methylene chloride to give 0.056 g of compound 1B as a yellow solid. HPLC: 100% at 3.497 min (retention time) (YMC S5 ODS column 4.6×50 mm eluting with 10–90% aqueous methanol over 4 minutes containing 0.2% phosphoric acid, 4 mL/min, monitoring at 220 nm). MS (ES): m/z 360.66 [M+Na]$^+$.

EXAMPLE 2

(3aα,4α,7α,7aα)-Octahydro-3-hydroxy-2-[4-nitro-3-(trifluoromethyl)phenyl]-4,7-methano-1H-isoindol-1-one (2)

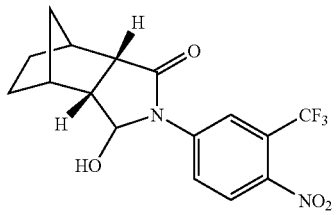

NaBH$_4$ (0.011 g, 0.282 mmol) was added to a solution of (3aα,4α,7α,7aα)-hexahydro-2-[4-nitro-3-(trifluoromethyl)phenyl]-4,7-methano-1H-isoindole-1,3(2H)-dione (0.100 g, 0.282 mmol, prepared as described in U.S. application Ser. No. 60/271,672) in THF/MeOH (2.0 mL/1.0 mL) at 0° C., and the reaction was slowly warmed to 25° C. After 1 h, the reaction was quenched with water and extracted with methylene chloride (3×30 mL). The combined organic layers were dried over anhydrous sodium sulfate and then concentrated in vacuo, to yield 0.096 g of compound 2 as a white solid. The crude material required no further purification. HPLC: 96% at 3.847 min (retention time) (YMC S5 ODS column 4.6×50 mm eluting with 10–90% aqueous methanol over 4 minutes containing 0.2% phosphoric acid, 4 mL/min, monitoring at 220 nm). MS (ES): m/z 357.06 [M+H]$^+$.

EXAMPLE 3

(3aα,4α,7α,7aα)-Octahydro-2-[4-nitro-3-(trifluoromethyl)phenyl]-4,7-methano-1H-isoindol-1-one (3)

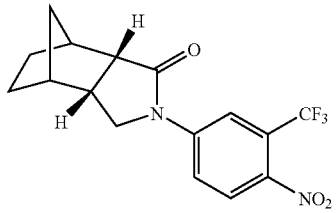

To a solution of compound 2 (0.050 g, 0.14 mmol) in methylene chloride (3.0 mL) at 0° C. was added TFA (0.150 mL) and triethylsilane (0.150 mL) and the reaction was slowly warmed to 25° C. After 1 h, the reaction was concentrated in vacuo and purified by preparative TLC on silica eluting with methylene chloride to give 0.040 g of compound 3 as a white solid. HPLC: 95% at 4.060 min (retention time) (YMC S5 ODS column 4.6×50 mm eluting with 10–90% aqueous methanol over 4 minutes containing 0.2% phosphoric acid, 4 mL/min, monitoring at 220 nm). MS (ES): m/z 341.15 [M+H]$^+$.

EXAMPLE 4

(3aα,4α,7α,7aα)-2,3,3a,4,7,7a-Hexahydro-3-hydroxy-2-[4-nitro-3-(trifluoromethyl)phenyl]-4,7-methano-1H-isoindol-1-one (4)

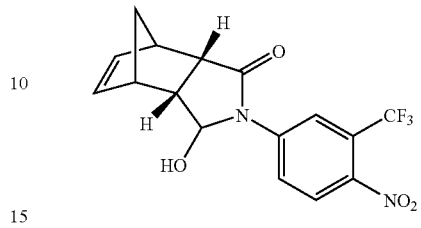

A solution of (3aα,4α,7α,7aα)-3a,4,7,7a-tetrahydro-2-[4-nitro-3-(trifluoromethyl)phenyl]-4,7-methano-1H-isoindole-1,3(2H)-dione (500 mg, 1.42 mmol, 1 eq, prepared as described in U.S. application Ser. No. 60/271,672) in THF (2 mL) was added to a solution of NaBH$_4$ (54 mg, 1.42 mmol, 1 eq) in THF (8 mL) and MeOH (4 mL) at 0° C. After 10 min, the reaction was warmed to rt and then stirred for 2 h. The reaction was quenched by the careful addition of water (4 mL) and extracted with CH$_2$Cl$_2$ (3×10 mL). The combined organic layers were washed with brine (1×25 mL) and dried over Na$_2$SO$_4$ to give compound 4 (480 mg, 1.36 mmol, 95.5%) as a yellow solid. HPLC conditions: 90% at 3.61 min (YMC 5 u Ballistic C18 4.6×50 mm, 10%–90% aqueous methanol over 4 minute gradient with 0.1% TFA, detecting at 220 nm). MS (ES): m/z 528.41 [M+H]$^+$.

EXAMPLE 5

(3aα,4α,7α,7aα)-2-[4-Bromo-3-(trifluoromethyl)phenyl]-2,3,3a,4,7,7a-hexahydro-3-methoxy-4,7-methano-1H-isoindol-1-one (5)

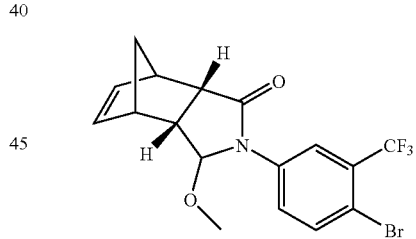

(3aα,4α,7α,7aα)-2-[4-Bromo-3-(trifluoromethyl)phenyl]-3a,4,7,7a-tetrahydro-4,7-methano-1H-isoindole-1,3(2H)-dione (0.200 g, 0.52 mmol, prepared as described in U.S. application Ser. No. 60/271,672) was dissolved in MeOH/THF (2 mL/4 mL) and cooled to 0° C. NaBH$_4$ was then added in one portion. After 10 min, the reaction was warmed to 25° C., stirred at rt for 1 h and then 12 N HCl (0.050 mL) was added. After 1 h, the reaction was quenched with sat. aq. NaHCO$_3$ (20 mL) and then extracted with methylene chloride (2×50 mL). The organic layers were dried over anhydrous sodium sulfate and then concentrated in vacuo to give 0.202 g of compound 5 as a white solid. HPLC: 91.5% at 4.140 min (retention time) (YMC S5 ODS column 4.6×50 mm eluting with 10–90% aqueous methanol over 4 minutes containing 0.2% phosphoric acid, 4 mL/min, monitoring at 220 nm). MS (ES): m/z 403.07 [M+H]$^+$.

EXAMPLE 6

(3aα,4α,7α,7aα)-Octahydro-2-[4-nitro-3-(trifluoromethyl)phenyl]-3-(2-propenyl)-4,7-methano-1H-isoindol-1-one (6)

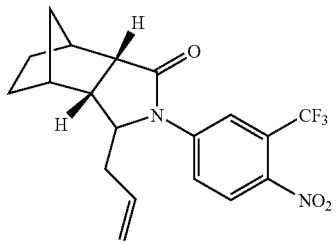

Compound 2 (0.100 g, 0.28 mmol) was suspended in methylene chloride (3.0 mL) and cooled to 0° C. BF$_3$.Et$_2$O (0.103 mL, 0.843 mmol) was then added and after 10 min of stirring, allyltrimethylsilane (0.053 mL, 0.336 mmol) was added. After 1 h, the reaction was quenched with saturated aqueous NaHCO$_3$ (20 mL) and then extracted with methylene chloride (3×30 mL). The organic layers were dried over anhydrous sodium sulfate and then concentrated in vacuo. The crude material was purified by preparative TLC on silica eluting with methylene chloride to give 0.029 g of compound 6 as a yellow oil. HPLC: 95% at 4.230 min (retention time) (YMC S5 ODS column 4.6×50 mm eluting with 10–90% aqueous methanol over 4 minutes containing 0.2% phosphoric acid, 4 mL/min, monitoring at 220 nm). MS (ES): m/z 381.16 [M+H]$^+$.

EXAMPLE 7

(3aα,4β,7β,7aβ)-Octahydro-3-hydroxy-2-(4-nitro-1-naphthalenyl)-4,7-epoxy-1H-isoindol-1-one (7)

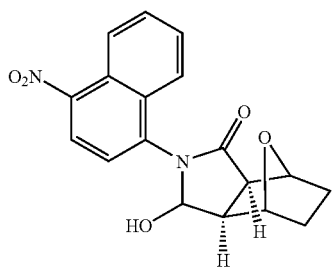

A solution of (3aα,4β,7β,7aα)-hexahydro-2-(4-nitro-1-naphthalenyl)-4,7-epoxy-1H-isoindole-1,3(2H)-dione (500 mg, 1.48 mmol, prepared as described in U.S. application Ser. No. 09/885,381) in THF (4.0 mL) was added to a solution of NaBH$_4$ (56 mg, 1.48 mmol, 1 eq) in 2:1 THF:MeOH (15 mL) at 0° C. Stirring was continued at 0° C. for 10 min and then at rt for 2 h. The reaction mixture was poured into H$_2$O (20 mL) and extracted with CH$_2$Cl$_2$ (2×15 mL). The combined organic layers were washed with brine (1×30 mL), dried over MgSO$_4$ and concentrated under reduced pressure. Purification by flash chromatography on silica gel eluting with 20% acetone/CH$_2$Cl$_2$ gave 192.4 mg (38%) of compound 7 as a yellow solid. HPLC: 96% at 1.29 min (YMC S5 TurboPack Pro column 4.6×33 mm, 10–90% aqueous methanol over 2 minutes containing 0.1% TFA, 4 mL/min, monitoring at 220 nm). MS (ES): m/z 341.0 [M+H]$^+$.

EXAMPLE 8

(3aα,4β,7β,7aα)-Octahydro-2-(4-nitro-1-naphthalenyl)-4,7-epoxy-1H-isoindol-1-one (8)

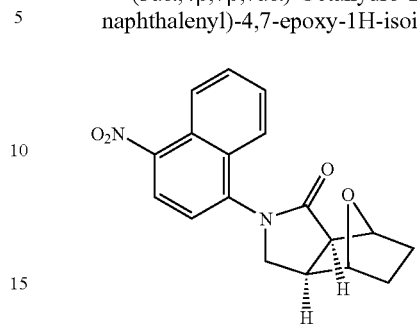

To a solution of compound 7 (162 mg, 0.48 mmol, 1 eq) in CH$_2$Cl$_2$ (5 mL) at 0° C. was added triethylsilane (1.25 mL) followed by TFA (1.25 mL). The reaction mixture was stirred at rt for 3 h, added to sat. NaHCO$_3$ (10 mL) and extracted with CH$_2$Cl$_2$ (2×10 mL). The combined organic layers were dried over Na$_2$SO$_4$ and concentrated under reduced pressure to give 152 mg (99%) compound 8 as an orange solid. HPLC: 99% at 3.28 min (YMC 5 u Ballistic C18 column 4.6×50 mm, 10–90% aqueous methanol over 4 minutes containing 0.1% TFA, 4 mL/min, monitoring at 220 nm). MS (ES): m/z 325.14 [M+H]$^+$.

EXAMPLE 9

(3aα,4α,7α,7aα)-2,3,3a,4,7,7a-Hexahydro-3-hydroxy-2-[3-(trifluoromethyl)phenyl]-4,7-ethano-1H-isoindol-1-one (9)

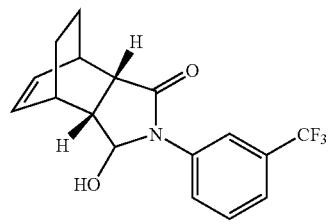

(3aα,4α,7α,7aα)-3a,4,7,7a-Tetrahydro-2-[3-(trifluoromethyl)phenyl]-4,7-ethano-1H-isoindole-1,3(2H)-dione (0.30 g, 0.93 mmol, prepared as described in U.S. application Ser. No. 60/271,672 incorporated herein by reference) was dissolved in THF (5 mL) and MeOH (2.5 mL), then was cooled to 0° C. NaBH$_4$ (0.035 g, 0.93 mmol) was added. The reaction mixture was stirred at 0° C. for 10 min and then warmed up to 22° C. for 2 h. Water was added and the aqueous layer was extracted with CH$_2$Cl$_2$ (3×30 mL). The organics were washed with brine and dried over anhydrous magnesium sulfate. Concentration gave 255 mg of the title compound 9 as a white solid. HPLC conditions: 98% at 3.20 min (YMC S5 ODS 4.6×50 mm, 10%–90% aqueous methanol over 4 minute containing 0.2% H$_3$PO$_4$, monitoring at 220 nm). MS (ES): m/z 324.19 [M+H]$^+$.

EXAMPLE 10

(3aα,4α,7α,7aα)-2,3,3a,4,7,7a-Hexahydro-2-[3-(trifluoromethyl)phenyl]-4,7-ethano-1H-isoindol-1-one (10)

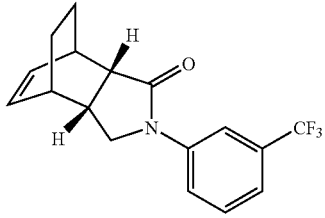

(3aα,4α,7α,7aα)-2,3,3a,4,7,7a-Hexahydro-3-hydroxy-2-[3-(trifluoro-methyl)phenyl]-4,7-ethano-1H-isoindol-1-one (0.025 mg, 0.70 mmol, prepared as described in U.S. application Ser. No. 60/271,672 incorporated herein by reference) was dissolved in CH$_2$Cl$_2$ (30 mL), then TFA (0.20 mL, 2.80 mmol) and Et$_3$SiH (0.45 mL, 2.8 mmol) were added. The reaction mixture was stirred at room temperature under N$_2$ for 5 h. Saturated NaHCO$_3$ (30 mL) was added and the mixture was extracted with CH$_2$Cl$_2$. The organic layer was separated and the combined organic layers were washed with brine and dried over anhydrous magnesium sulfate. The solvent was concentrated and the resulting oil was purified by flash column on SiO$_2$, eluting with 1% MeOH/CH$_2$Cl$_2$, to give 197 mg of the title compound 10 as a white solid. HPLC conditions: 98% at 3.62 min (YMC S5 ODS 4.6×50 mm, 10%–90% aqueous methanol over 4 minute gradient with 0.2% H$_3$PO$_4$, monitoring at 220 nm). MS (ES): m/z 308.21 [M+H]$^+$.

EXAMPLE 11

(3aα,4α,7α,7aα)-Octahydro-3a-hydroxy-2-[4-nitro-3-(trifluoromethyl)phenyl]-4,7-ethano-3H-indazol-3-one (11G)

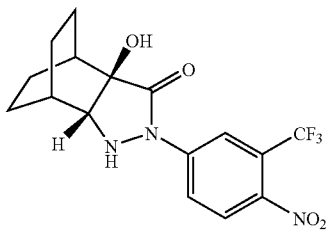

A. Bicyclo[2.2.2]octa-2,5-diene-2-carboxylic acid (11A)

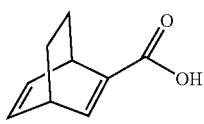

Compound 11A was made according to the procedure of Pitha, J.; et. al. *J. Med. Chem.*, 32, 96–100 (1989). A mixture of cyclohexadiene (3.90 g, 48.6 mmol) and propiolic acid (2.35 g, 33.5 mmol, 1 eq) was stirred at rt for 1 week. Purification by flash chromatography on silica gel eluting with 2% MeOH/CHCl$_3$ gave 2.07 g (41%) of 11A as a yellow solid.

B. Bicyclo[2.2.2]oct-2-ene-2-carboxylic acid (11B)

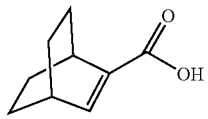

Compound 11A (600 mg, 3.99 mmol) was dissolved in EtOAc (5 mL), 5% Pd/C (12 mg) was added and the mixture was stirred under a hydrogen balloon for 1.5 h. The reaction mixture was filtered through a pad of celite and concentrated under reduced pressure to give 600 mg of compound 11B as a yellow oil. No further purification was necessary. HPLC conditions: 95% at 2.65 min (YMC S5 ODS 4.6×50 mm, 10%–90% aqueous methanol over 4 minute gradient with 0.2% H$_3$PO$_4$, detecting at 220 nm).

C. Bicyclo[2.2.2]oct-2-ene-2-carbonyl chloride (11C)

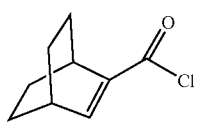

Oxalyl chloride (2.0 M in CH$_2$Cl$_2$, 2.4 mL, 4.8 mmol, 1.2 eq) was added to a solution of compound 11B (600 mg, 3.95 mmol, 1 eq) in CH$_2$Cl$_2$ (8 mL) containing one drop of DMF. The reaction mixture was stirred at rt for 3 h and then concentrated under reduced pressure to give 680 mg of compound 11C which was used in the next step without purification.

D. Bicyclo[2.2.2]oct-2-ene-2-carboxylic acid (4-nitro-3-trifluoromethylphenyl)-amide (11D)

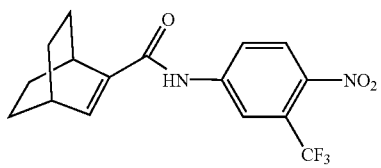

4-Nitro-3-trifluoroaniline (542 mg, 2.63 mmol, 1 eq) was added to NaH (60% in mineral oil, 105 mg, 2.63 mmol, 1 eq) in THF (2 mL). The reaction mixture was stirred at rt for 2 h and then a solution of compound 11C (447 mg, 2.63 mmol, 1 eq) in THF (4 mL) was added. The reaction mixture was stirred at rt overnight and then quenched by careful addition of water (5 mL) and extracted with CH$_2$Cl$_2$ (2×20 mL). The combined organic layers were washed with brine (1×25 mL), dried over Na$_2$SO$_4$ and concentrated under reduced pressure. Purification by flash chromatography on silica gel eluting with 30% EtOAc/hexane gave 360 mg (1.06 mmol, 40.3%) of compound 11D.

E. 3-Oxa-tricyclo[3.2.2.0$^{2,4}$]nonane-2-carboxylic acid (4-nitro-3-trifluoromethyl-phenyl)-amide (11E)

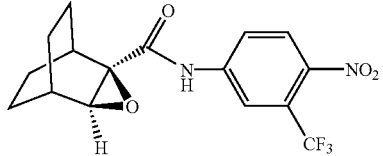

mCPBA (60% mixture, 518 mg, 3.00 mmol, 3 eq) was added to a solution of 11D (340 mg, 1.0 mmol, 1.0 eq) in CH$_2$Cl$_2$ (20 mL). The reaction mixture was stirred at rt overnight and then diluted with CH$_2$Cl$_2$ (40 mL). The organic solution was washed with sat. NaHCO$_3$ (1×50 mL), brine (1×50 mL), dried over Na$_2$SO$_4$ and concentrated under reduced pressure. Purification by flash chromatography on silica gel eluting with 80% CH$_2$Cl$_2$/hexane gave 205 mg (0.58 mmol, 57.6%) of compound 11E. HPLC conditions: 95% at 3.70 min (YMC S5 ODS 4.6×50 mm, 10%–90% aqueous methanol over 4 minute gradient with 0.2% H$_3$PO$_4$, detecting at 220 nm).

F. 3-Oxa-tricyclo[3.2.2.0$^{2,4}$]nonane-2-carboxylic acid N-(4-nitro-3-trifluoromethyl-phenyl)-hydrazide (11F)

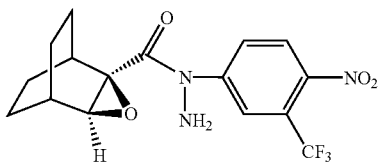

NaH (60% in mineral oil, 7.9 mg, 0.20 mmol, 1.4 eq) was added to the solution of 11E (50 mg, 0.14 mmol, 1 eq) in DMF (3 mL). The reaction mixture was heated at 70° C. for 2 h. The reaction was cooled to rt and diphenylphosphinyl-hydroxylamine (52 mg, 0.22 mmol, 1.6 eq, made according to the procedure of Colvin, E. W. et. al. *Tetrahedron Lett.* 23, 3835–6 (1982)) was added. The reaction mixture was stirred at rt overnight and quenched by addition of water (3 mL) and extracted with EtOAc (2×20 mL). The combined organics were washed with H$_2$O (25 mL), dried over Na$_2$SO$_4$ and concentrated under reduced pressure. Purification by flash chromatography on silica gel eluting with 10% EtOAc/CH$_2$Cl$_2$ gave 8.0 mg (0.022 mmol, 15.4%) of compound 11F as a yellow solid. HPLC conditions: 93% at 3.54 min (YMC S5 ODS 4.6×50 mm, 10%–90% aqueous methanol over 4 minute gradient with 0.2% H$_3$PO$_4$, detecting at 220 nm).

G. (3aα,4α,7α,7aα)-Octahydro-3a-hydroxy-2-[4-nitro-3-(trifluoromethyl)phenyl]-4,7-ethano-3H-indazol-3-one (11G)

The solution of 11F (8.0 mg, 0.022 mmol) in EtOH (1 mL) was heated at 65° C. overnight. The solvent was removed under reduced pressure to give 11G (7.2 mg, 0.019 mmol, 90%). HPLC conditions: 97% at 3.54 min (YMC S5 ODS 4.6×50 mm, 10%–90% aqueous methanol over 4 minute gradient with 0.2% H$_3$PO$_4$, detecting at 220 nm). MS (ES): m/z 369.9 [M+H]$^+$.

EXAMPLE 12

(1α,3aα,4α,7α,7aα)-2,3,3a,4,7,7a-Hexahydro-2-(4-nitro-1-naphthalenyl)-3-oxo-4,7-methano-1H-isoindole-1-carbonitrile (12B)

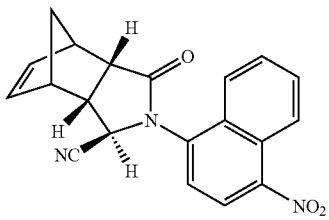

A. (1α,3aα,4α,7α,7aα)-2,3,3a,4,7,7a-Hexahydro-3-hydroxy-2-(4-nitro-1-naphthalenyl)-4,7-methano-1H-isoindole-1-one (12A)

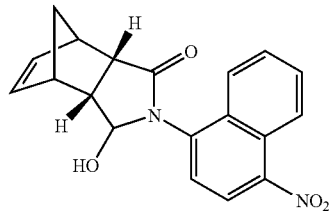

(3aα,4α,7α,7aα)-3a,4,7,7a-Tetrahydro-2-(4-nitro-1-naphthalenyl)-4,7-methano-1H-isoindole-1,3(2H)-dione (1.00 g, 2.99 mmol, prepared as described in U.S. application Ser. No. 60/271,672) was dissolved in THF/MeOH (15 mL/15 mL) and the solution was cooled to 0° C. Sodium borohydride (0.113 g, 2.99 mmol) was then added followed by slow warming to 25° C. After 4 h, the reaction was quenched with water (20 mL) and extracted with methylene chloride (3×50 mL). The combined organics were dried over anhydrous sodium sulfate and concentrated in vacuo to give 0.895 g of compound 12A as an orange solid. This compound was taken on without purification.

B. (3aα,4α,7α,7aα)-2,3,3a,4,7,7a-Hexahydro-2-(4-nitro-1-naphthalenyl)-3-oxo-4,7-methano-1H-isoindole-1-carbonitrile (12B)

Compound 12A (0.140 g, 0.417 mmol) was dissolved in methylene chloride (4.0 mL) and cooled to −78° C. BF$_3$.Et$_2$O (0.153 mL, 1.25 mmol) was then added followed by trimethylsilylcyanide (0.167 mL, 1.25 mmol). The reaction was then slowly warmed to 25° C. After 2 h, the reaction was quenched with saturated aqueous NaHCO$_3$ (30 mL) and then extracted with methylene chloride (3×30 mL). The combined organics were dried over anhydrous sodium sulfate and then concentrated in vacuo. The crude product was purified by preparative TLC on silica gel, eluting with 10% acetone in chloroform, to give 0.093 g of compound 12B as a white solid. HPLC: 98% at 2.747 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 346.17 [M+H]$^+$.

EXAMPLE 13

(3aα,4β,7β,7aα)-2,3,3a,4,7,7a-Hexahydro-3-hydroxy-4,7-dimethyl-2-[3-(trifluoromethyl)phenyl]-4,7-epoxy-1H-isoindol-1-one (13B)

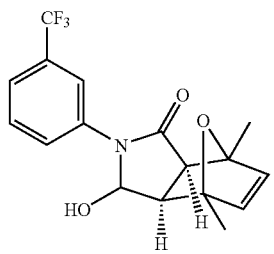

A. (3aα,4β,7β,7aα)-3a,4,7,7a-Tetrahydro-4,7-dimethyl-2-[3-(trifluoromethyl)phenyl]-4,7-epoxy-1H-isoindole-1,3(2H)-dione & (3aα,4α,7α,7aα)-3a,4,7,7a-Tetrahydro-4,7-dimethyl-2-[3-(trifluoromethyl)phenyl]-4,7-epoxy-1H-isoindole-1,3(2H)-dione (13Ai & 13Aii)

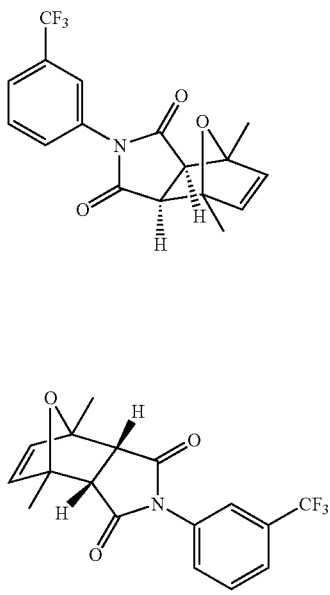

2,5-Dimethylfuran (0.32 mL, 2.6 mmol) and 1-[3-(trifluoromethyl)phenyl]-1H-pyrrole-2,5-dione (0.50 g, 2.5 mmol) were dissolved in dichloromethane (2.0 mL). The reaction mixture was stirred at 22° C. for 16 h and then the solvent was removed in vacuo. The crude material was purified by flash chromatography on silica gel, eluting with 0.5% MeOH/CH$_2$Cl$_2$, to give 50 mg of compound 13Aii as a white solid and 250 mg of compound 13Ai as white solid. HPLC conditions: 95% at 3.05 min (YMC S5 ODS 4.6×50 mm, 10%–90% aqueous methanol over 4 minute gradient with 0.2% H$_3$PO$_4$, detecting at 220 nm). MS (ES): m/z 340.19 [M+H]$^+$.

B. (3aα,4β,7β,7aα)-2,3,3a,4,7,7a-Hexahydro-3-hydroxy-4,7-dimethyl-2-[3-(trifluoromethyl)phenyl]-4,7-epoxy-1H-isoindol-1-one (13B)

Compound 13Ai (150 mg, 0.442 mmol) was dissolved in THF (2 mL) and MeOH (1 mL), then was cooled to 0° C. NaBH$_4$ (18.5 mg, 0.487 mmol) was added, the reaction mixture was stirred at 0° C. for 10 min and then warmed to 22° C. for 2 h. Water was then added and the aqueous layer was extracted with dichloromethane (3×10 mL). The organics were washed with brine and dried over anhydrous magnesium sulfate. Concentration gave 145 mg of compound 13B as a white solid. HPLC conditions: 97% at 2.78 min (YMC S5 ODS 4.6×50 mm, 10%–90% aqueous methanol over 4 minute gradient with 0.2% H$_3$PO$_4$, detecting at 220 nm). MS (ES): m/z 342.19 [M+H]$^+$.

EXAMPLE 14

(3aα,4β,7β,7aα)-Octahydro-3-hydroxy-4,7-dimethyl-2-[3-(trifluoromethyl)phenyl]-4,7-epoxy-1H-isoindol-1-one (14)

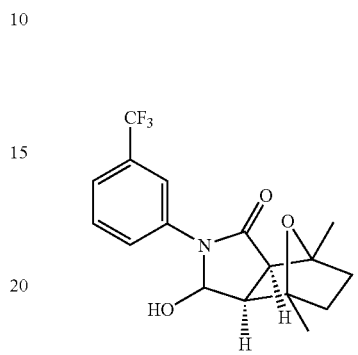

Compound 13B (100 mg, 0.293 mmol) was dissolved in EtOH/EtOAc (2 mL/2 mL) and 10% Pd/C (70 mg) was added. The reaction mixture was stirred at room temperature under H$_2$ balloon for 16 h and then filtered through celite. Concentration gave 97 mg of compound 14 as a white solid. HPLC conditions: 97% at 2.78 min (YMC S5 ODS 4.6×50 mm, 10%–90% aqueous methanol over 4 minute gradient with 0.2% H$_3$PO$_4$, detecting at 220 nm). MS (ES): m/z 344.21 [M+H]$^+$.

EXAMPLES 15 TO 30

Additional compounds of the present invention were prepared by procedures analogous to those described above. The compounds of Examples 15 to 30 having the structures shown, the compound name, retention time, molecular mass, and the procedure employed, are set forth in Table 1. The absolute configuration for the following compounds was not determined and all chiral compounds were prepared as racemates.

The chromatography techniques used to determine the compound retention times of Table 1 are as follows: LCMS= YMC S5 ODS column, 4.6×50 mm eluting with 10–90% MeOH/H$_2$O over 4 minutes containing 0.1% TFA; 4 mL/min, monitoring at 220 nm. LCMS*=YMC S5 ODS column, 4.6×50 mm eluting with 10–90% MeOH/H$_2$O over 2 minutes containing 0.1% TFA; 4 mL/min, monitoring at 220 nm. LC=YMC S5 ODS column 4.6×50 mm eluting with 10–90% MeOH/H$_2$O over 4 minutes containing 0.2% phosphoric acid, 4 mL/min, monitoring at 220 nm. The molecular mass of the compounds listed in Table 1 were determined by MS (ES) by the formula m/z.

TABLE 1

| Ex. No. | Structure | Compound Name | Retention Time Min. | Procedure of Example |
|---|---|---|---|---|
| 15 | 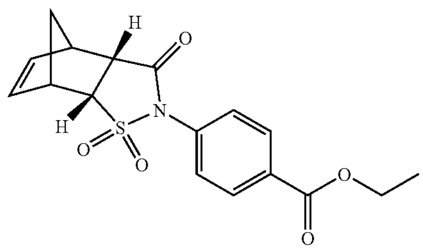 | (3aα,4α,7α,7aα)-4-(2,3,3a,4,7,7a-Hexahydro-1,1-dioxido-3-oxo-4,7-methano-1,2-benzisothiazol-2-yl)benzoic acid, ethyl ester | 3.427 LC | 1 |
| 16 | 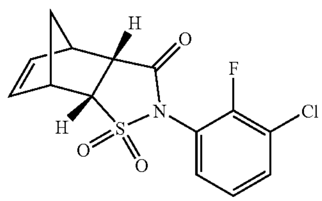 | (3aα,4α,7α,7aα)-2-(3-Chloro-2-fluorophenyl)-3a,7,7,7a-tetrahydro-4,7-methano-1,2-benzisothiazol-3(2H)-one,1,1-dioxide | 3.37 LC | 1 |
| 17 | 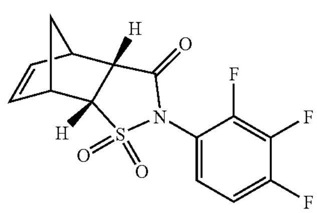 | (3aα,4α,7α,7aα)-3a,4,7,7a-Tetrahydro-2-(2,3,4-trifluorophenyl)-4,7-methano-1,2-benzisothiazol-3(2H)-one,1,1-dioxide | 3.41 LC | 1 |
| 18 | 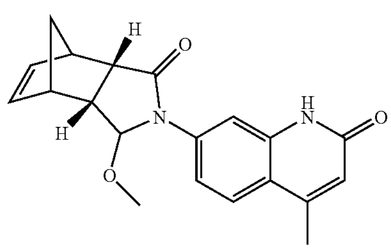 | (3aα,4α,7α,7aα)-2-(1,2-Dihydro-4-methyl-2-oxo-7-quinolinyl)-2,3,3a,4,7,7a-hexahydro-3-methoxy-4,7-methano-1H-isoindol-1-one | 2.95 & 3.20 Atrop Isomers LC [M + H]$^+$ 337.33 | 5 |
| 19 | 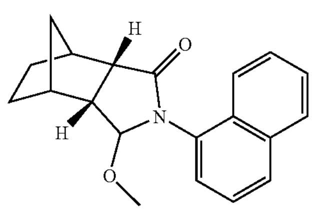 | (3aα,4α,7α,7aα)-Octahydro-3-methoxy-2-(1-naphthalenyl)-4,7-methano-1H-isoindol-1-one | 4.19 LC [M + H]$^+$ 307.99 | 5 |
| 20 | 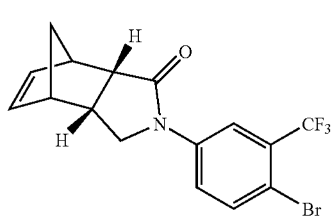 | (3aα,4α,7α,7aα)-2-[4-Bromo-3-(trifluoromethyl)phenyl]-2,3,3a,4,7,7a-hexahydro-4,7-methano-1H-isoindol-1-one | 3.75 LC [M + H]$^+$ 372.25 | 3 |

TABLE 1-continued

| Ex. No. | Structure | Compound Name | Retention Time Min. | Procedure of Example |
|---|---|---|---|---|
| 21 | 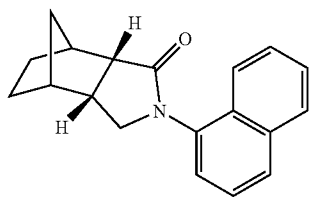 | (3aα,4α,7α,7aα)-Octahydro-2-(1-naphthalenyl)-4,7-methano-1H-isoindol-1-one | 3.87 LC [M + H]$^+$ 278.25 | 3 |
| 22 | 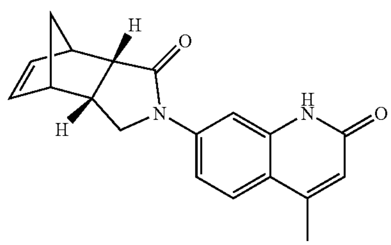 | (3aα,4α,7α,7aα)-2-(1,2-Dihydro-4-methyl-2-oxo-7-quinolinyl)-2,3,3a,4,7,7a-hexahydro-4,7-methano-1H-isoindol-1-one | 3.41 LC [M + H]$^+$ 307.25 | 3 |
| 23 | 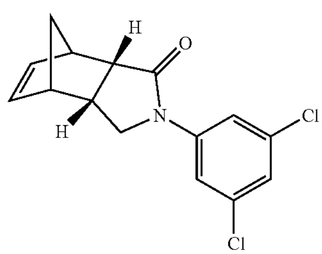 | (3aα,4α,7α,7aα)-2-(3,5-Dichlorophenyl)-2,3,3a,4,7,7a-hexahydro-4,7-methano-1H-isoindol-1-one | 4.30 LC | 3 |
| 24 | 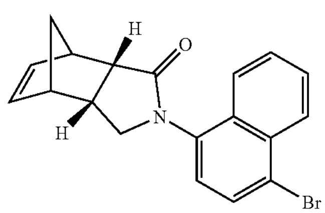 | (3aα,4α,7α,7aα)-2-(4-Bromo-1-naphthalenyl)-2,3,3a,4,7,7a-hexahydro-4,7-methano-1H-isoindol-1-one | 4.14 LC | 3 |
| 25 | 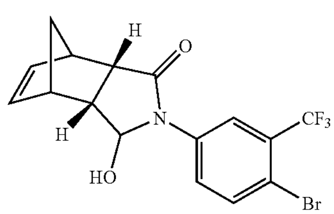 | (3aα,4α,7α,7aα)-2-[4-Bromo-3-(trifluoromethyl)phenyl]-2,3,3a,4,7,7a-hexahydro-3-hydroxy-4,7-methano-1H-isoindol-1-one | 3.82 LC | 2 |
| 26 | 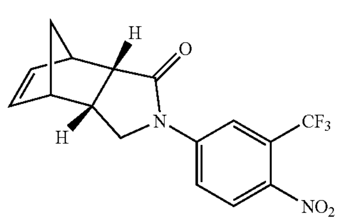 | (3aα,4α,7α,7aα)-2,3,3a,4,7,7a-Hexahydro-2-[4-nitro-3-(trifluoromethyl)phenyl]-4,7-methano-1H-isoindol-1-one | 3.86 LC | 3 |

TABLE 1-continued

| Ex. No. | Structure | Compound Name | Retention Time Min. | Procedure of Example |
|---|---|---|---|---|
| 27 | 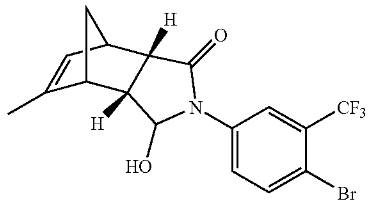 | (3aα,4α,7α,7aα)-2-[4-Bromo-3-(trifluoromethyl)phenyl]-2,3,3a,4,7,7a-hexahydro-3-hydroxy-5-methyl-4,7-methano-1H-isoindol-1-one | 3.67 LC | 2 |
| 28 | 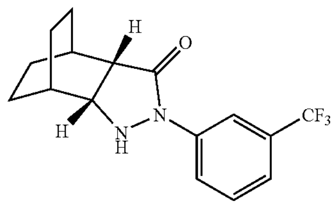 | (3aα,4α,7α,7aα)-Octahydro-3a-hydroxy-2-[3-(trifluoromethyl)phenyl]-4,7-ethano-3H-indazol-3-one | 3.43 LC | 11 |
| 29 | 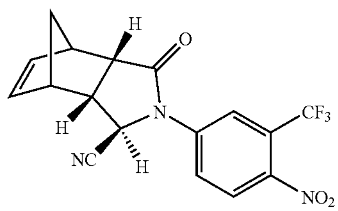 | (1α,3aα,4α,7α,7aα)-2,3,3a,4,7,7a-Hexahydro-2-[4-nitro-3-(trifluoromethyl)phenyl]-3-oxo-4,7-methano-1H-isoindole-1-carbonitrile | 3.17 LC | 12 |
| 30 | 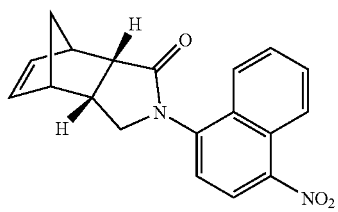 | (3aα,4α,7α,7aα)-2,3,3a,4,7,7a-Hexahydro-2-(4-nitro-1-naphthalenyl)-4,7-methano-1H-isoindol-1-one | 3.16 LC | 3 |

We claim:
1. A compound of the following formula, or a salt thereof:

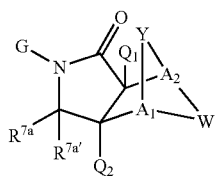

wherein the symbols have the following meanings and are, for each occurrence, independently selected:
G is an aryl or heteroaryl group, where said group is mono- or polycyclic and is optionally substituted at one or more positions;
$A_1$ is $CR^7$;
$A_2$ is $CR^7$;
Y is O, S, or $(CR^7R^{7'})_n$ wherein n=1 or 2;
W is $CR^7R^{7'}$—$CR^7R^{7'}$ or $CR^8$=$CR^{8'}$;
$Q_1$ is H, alkyl or substituted alkyl;
$Q_2$ is H, alkyl or substituted alkyl;
$R^1$ and $R^{1'}$ are each independently selected from H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, and/or arylalkyl or substituted arylalkyl;
$R^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;
$R^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C$=O, $R^1NHC$=O, $R^1OC$=O; $SO_2OR^1$, or $SO_2NR^1R^{1'}$;

R[5] is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, R[1]C=O, R[1]NHC=O, SO$_2$R[1], SO$_2$OR[1], or SO$_2$NR[1]R[1'];

R[7] and R[7'] are at each occurrence independently selected from H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, N$_3$, CN, OR[1], O(C=O)R[1], O(C=O)NHR[1], O(C=O)OR[1], nitro, hydroxylamine, hydroxylamide, amino, SR[1], SeR[1], NHR[4], NR[2]R[5], NOR[1], thiol, alkylthio or substituted alkylthio, R[1]C=O, R[1]OC=O, R[1]NHC=O, SO$_2$R[1], SOR[1], PO$_3$R[1]R[1'], R[1]R[1']NC=O, C=OSR[1], SO$_2$R[1], SO$_2$OR[1], SO$_2$NR[1]R[1'], OSO$_2$-aryl, OSO$_2$-(substituted aryl), OSO$_2$-heterocyclo, OSO$_2$-(substituted heterocyclo), and/or COCl;

R[8] and R[8'] are each independently selected from H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, OR[1], amino, NHR[4], NR[2]R[5], NOR[1], alkylthio or substituted alkylthio, C=OSR[1], R[1]OC=O, R[1]C=O, R[1]NHC=O, R[1]R[1']NC=O, SO$_2$OR[1], S=OR[1], SO$_2$R[1], PO$_3$R[1]R[1'], and/or SO$_2$NR[1]R[1'];

with the proviso that when A$_1$ and A$_2$ are CH; Y is O or CH$_2$; W is CH$_2$—CH$_2$ or CH=CH; Q$_2$ is H or CH$_2$OH; and Q$_2$ is H or CH$_2$OH, then (i) G is not pyridinyl, phenyl, dichlorophenyl, bromophenyl or methoxyphenyl when R[7a] or R[7a'] is OH or OCH$_3$ and (ii) G is not methoxyphenyl or phenyl substituted with —OCH$_2$CH$_2$-SB where SB is dimethylamino, diethylamino, piperidinyl, morpholinyl, or pyrrolidinyl when R[7a] and R[7a'] are both hydrogen.

2. A compound of selected from the group consisting of (i):

(3aα,4α,7α,7aα)-Octahydro-3-hydroxy-2-[4-nitro-3-(trifluoromethyl)phenyl]-4,7-methano-1H-isoindol-1-one (2);

(3aα,4α,7α,7aα)-Octahydro-2-[4-nitro-3-(trifluoromethyl)phenyl]-4,7-methano-1H-isoindol-1-one (3);

(3aα,4α,7α,7aα)-2,3,3a,4,7,7a-Hexahydro-3-hydroxy-2-[4-nitro-3-(trifluoromethyl)phenyl]-4,7-methano-1H-isoindol-1-one (4);

(3aα,4α,7α,7aα)-2-[4-Bromo-3-(trifluoromethyl)phenyl]-2,3,3a,4,7,7a-hexahydro-3-methoxy-4,7-methano-1H-isoindol-1-one (5);

(3aα,4α,7α,7aα)-Octahydro-2-[4-nitro-3-(trifluoromethyl)phenyl]-3-(2-propenyl)-4,7-methano-1H-isoindol-1-one (6);

(3aα,4β,7β,7aα)-Octahydro-3-hydroxy-2-(4-nitro-1-naphthalenyl)-4,7-epoxy-1H-isoindol-1-one (7);

(3aα,4β,7β,7aα)-Octahydro-2-(4-nitro-1-naphthalenyl)-4,7-epoxy-1H-isoindol-1-one (8);

(3aα,4α,7α,7aα)-2,3,3a,4,7,7a-Hexahydro-3-hydroxy-2-[3-(trifluoromethyl)phenyl]-4,7-ethano-1H-isoindol-1-one (9);

(3aα,4α,7α,7aα)-2,3,3a,4,7,7a-Hexahydro-2-[3-(trifluoromethyl)phenyl]-4,7-ethano-1H-isoindol-1-one (10);

(1α,3aα,4α,7α,7aα)-2,3,3a,4,7,7a-Hexahydro-2-(4-nitro-1-naphthalenyl)-3-oxo-4,7-methano-1H-isoindole-1-carbonitrile (12B);

(3aα,4β,7β,7aα)-2,3,3a,4,7,7a-Hexahydro-3-hydroxy-4,7-dimethyl-2-[3-(trifluoromethyl)phenyl]-4,7-epoxy-1H-isoindol-1-one (13B);

(3aα,4β,7β,7aα)-Octahydro-3-hydroxy-4,7-dimethyl-2-[3-(trifluoromethyl)phenyl]-4,7-epoxy-1H-isoindol-1-one (14);

(3aα,4α,7α,7aα)-2-(1,2-Dihydro-4-methyl-2-oxo-7-quinolinyl)-2,3,3a,4,7,7a-hexahydro-3-methoxy-4,7-methano-1H-isoindol-1-one;

(3aα,4α,7α,7aα)-Octahydro-3-methoxy-2-(1-naphthalenyl)-4,7-methano-1H-isoindol-1-one;

(3aα,4α,7α,7aα)-2-[4-Bromo-3-(trifluoromethyl)phenyl]-2,3,3a,4,7,7a-hexahydro-4,7-methano-1H-isoindol-1-one;

(3aα,4α,7α,7aα)-Octahydro-2-(1-naphthalenyl)-4,7-methano-1H-isoindol-1-one;

(3aα,4α,7α,7aα)-2-(1,2-Dihydro-4-methyl-2-oxo-7-quinolinyl)-2,3,3a,4,7,7a-hexahydro-4,7-methano-1H-isoindol-1-one;

(3aα,4α,7α,7aα)-2-(3,5-Dichlorophenyl)-2,3,3a,4,7,7a-hexahydro-4,7-methano-1H-isoindol-1-one;

(3aα,4α,7α,7aα)-2-(4-Bromo-1-naphthalenyl)-2,3,3a,4,7,7a-hexahydro-4,7-methano-1H-isoindol-1-one;

(3aα,4α,7α,7aα)-2-[4-Bromo-3-(trifluoromethyl)phenyl]-2,3,3a,4,7,7a-hexahydro-3-hydroxy-4,7-methano-1H-isoindol-1-one;

(3aα,4α,7α,7aα)-2,3,3a,4,7,7a-Hexahydro-2-[4-nitro-3-(trifluoromethyl)phenyl]-4,7-methano-1H-isoindol-1-one;

(3aα,4α,7α,7aα)-2-[4-Bromo-3-(trifluoromethyl)phenyl]-2,3,3a,4,7,7a-hexahydro-3-hydroxy-5-methyl-4,7-methano-1H-isoindol-1-one;

(1α,3aα,4α,7α,7aα)-2,3,3a,4,7,7a-Hexahydro-2-[4-nitro-3-(trifluoromethyl)phenyl]-3-oxo-4,7-methano-1H-isoindole-1-carbonitrile; and (3aα,4α,7α,7aα)-2,3,3a,4,7,7a-Hexahydro-2-(4-nitro-1-naphthalenyl)-4,7-methano-1H-isoindol-1-one; and (ii) a pharmaceutically acceptable salt.

3. A process for preparing a compound of the following formula XIV:

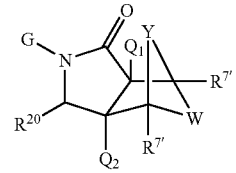

wherein G, Y, W, Q$_1$, Q$_2$, R[7], and R[7'] are as defined in claim 1, and $R^{20}$ is

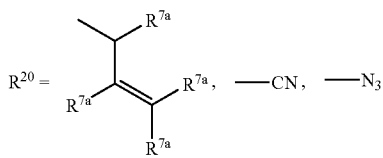

where the $R^{7a}$ groups are independently selected from those groups included in the definition of $R^7$, comprising the step of contacting a compound of the following formula X:

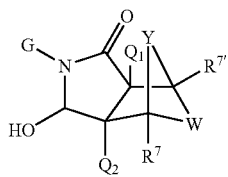

with a Lewis acid and a compound of the formula $(R^1)_3SiR^{20}$.

4. A compound according to claim 1, or a pharmaceutically-acceptable salt thereof, wherein at least one of $A_1$ and $A_2$ is —C(CH$_3$).

5. A compound according to claim 1, or a pharmaceutically-acceptable salt thereof, wherein G is phenyl or napthyl and said group G substituted with one, two or three substituents selected from trifluoromethyl, halogen, cyano, nitro, and/or lower alkyl.

6. A compound according to claim 1, or a pharmaceutically-acceptable salt thereof, wherein G is a group,

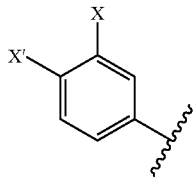

wherein X is trifluoromethyl or cyano and X' is trifluoromethyl, halogen, cyano, nitro, or lower alkyl.

7. A compound according to claim 1, or a pharmaceutically-acceptable salt thereof, wherein Y is O.

8. A compound according to claim 1, or a pharmaceutically-acceptable salt thereof, wherein $R^7$, and $R^{7'}$, $R^{7a}$ and $R^{7a'}$ are each independently selected from H, alkyl, OH, O(alkyl), alkenyl, cyano, O(C=O)R$^1$, O(C=O)NHR$^1$, O(C=O)OR$^1$, nitro, amino, SR$^1$, NHR$^4$, alkylthio, R$^1$C=O, R$^1$OC=O, R$^1$NHC=O, SO$_2$R$^1$, SOR$^1$, SO$_2$NR$^1$R$^{1'}$, OSO$_2$-aryl, OSO$_2$-(substituted aryl), OSO$_2$-heterocyclo, OSO$_2$-(substituted heterocyclo), and/or COCl.

9. A compound according to claim 1, having the formula,

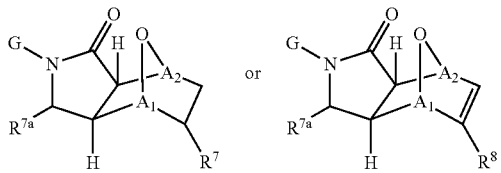

wherein $R^7$, $R^{7'}$, $R^{7a}$, and $R^8$ are at each occurrence independently selected from H, alkyl, OH, O(alkyl), alkenyl, cyano, O(C=O)R$^1$, nitro, amino, SR$^1$, NHR$^4$, alkylthio, R$^1$C=O, R$^1$OC=O, R$^1$NHC=O, SO$_2$R$^1$, SOR$^1$, SO$_2$NR$^1$R$^{1'}$, OSO$_2$-aryl, OSO$_2$-(substituted aryl), OSO$_2$-heterocyclo, OSO$_2$-(substituted heterocyclo), and/or COCl; or a pharmaceutically-acceptable salt thereof.

10. A compound according to claim 9, or a pharmaceutically-acceptable salt thereof, wherein at least one of $A_1$ and $A_2$ is —C(alkyl).

11. A compound according to claim 9, or a pharmaceutically-acceptable salt thereof, wherein $A_1$ and $A_2$ are both —C(CH$_3$).

12. A compound according to claim 9, or a pharmaceutically-acceptable salt thereof, wherein G is phenyl or napthyl and said group G is substituted with one, two or three substituents selected from trifluoromethyl, halogen, cyano, nitro, and/or lower alkyl.

13. A compound according to claim 9, or a pharmaceutically-acceptable salt thereof, wherein G is a group,

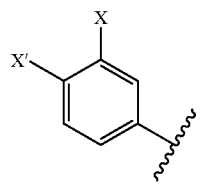

wherein X is trifluoromethyl or cyano and X' is trifluoromethyl, halogen, cyano, nitro, or lower alkyl.

14. A compound according to claim 1, having the formula,

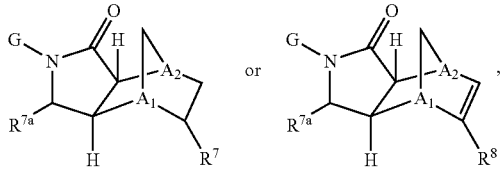

wherein $R^7$, $R^{7'}$, $R^{7a}$, and $R^8$ are at each occurrence independently selected from H, alkyl, OH, O(alkyl), alkenyl, cyano, O(C=O)R$^1$, nitro, amino, SR$^1$, NHR$^1$, alkylthio, R$^1$C=O, R$^1$OC=O, R$^1$NHC=O, SO$_2$R$^1$, SOR$^1$, SO$_2$NR$^1$R$^{1'}$, OSO$_2$-aryl, OSO$_2$-(substituted aryl), OSO$_2$-heterocyclo, OSO$_2$-(substituted heterocyclo), and/or COCl; or a pharmaceutically-acceptable salt.

15. A compound according to claim 14, or a pharmaceutically-acceptable salt thereof, wherein at least one of $A_1$ and $A_2$ is —C(alkyl).

16. A compound according to claim 14, or a pharmaceutically-acceptable salt thereof, wherein $A_1$ and $A_2$ are both —C(CH$_3$).

17. A compound according to claim 14, or a pharmaceutically-acceptable salt thereof, wherein G is phenyl or napthyl and said group G is substituted with one, two or three substituents selected from trifluoromethyl, halogen, cyano, nitro, and/or lower alkyl.

18. A compound according to claim 14, or a pharmaceutically-acceptable salt thereof, wherein G is a group,

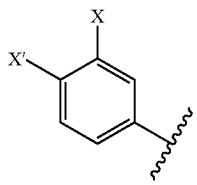

wherein X is trifluoromethyl or cyano and X' is trifluoromethyl, halogen, cyano, nitro, or lower alkyl.

19. A compound having the formula,

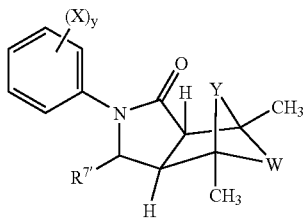

wherein,

Y is —O—, —S—, —CR$^{7'}$R$^{7'}$—, or —(CR$^{7'}$R$^{7'}$)$_2$—;

W is —CR$^7$R$^{7'}$—CR$^7$R$^{7'}$— or —CR$^8$=CR$^{8'}$—;

R$^7$ and R$^8$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, N$_3$, CN, OR$^1$, O(C=O)R$^1$, O(C=O)NHR$^1$, O(C=O)OR$^1$, nitro, hydroxylamine, hydroxylamide, amino, SR$^1$, NR$^4$R$^5$, alkylthio or substituted alkylthio, R$^1$C=O, R$^1$OC=O, R$^1$NHC=O, SO$_2$R$^1$, SOR$^1$, SO$_2$NR$^1$R$^{1'}$, OSO$_2$-aryl, OSO$_2$-(substituted aryl), OSO$_2$-heterocyclo, OSO$_2$-(substituted heterocyclo), or COCl;

R$^{7'}$ and R$^{8'}$ are at each occurrence independently selected from H, alkyl, substituted alkyl, OH, O(alkyl), alkenyl, and/or cyano;

R$^1$ and R$^{1'}$ are independently selected from H, alkyl or substituted alkyl, cycloalkyl or substituted cycloalkyl, heterocyclo or substituted heterocyclo, cycloalkylalkyl or substituted cycloalkyalkyl, heterocycloalkyl or substituted heterocycloalkyl, aryl or substituted aryl, and arylalkyl or substituted arylalkyl;

R$^4$ and R$^5$ are independently selected from H, alkyl or substituted alkyl, cycloalkyl or substituted cycloalkyl, heterocyclo or substituted heterocyclo, cycloalkylalkyl or substituted cycloalkylalkyl, heterocycloalkyl or substituted heterocycloalkyl, aryl or substituted aryl, arylalkyl or substituted arylalkyl, R$^1$C=O, R$^1$NHC=O, R$^1$OC=O; SO$_2$OR$^1$, and SO$_2$NR$^1$R$^{1'}$;

X is selected from trifluoromethyl, halogen, cyano, nitro, and/or alkyl; and y is 0, 1, 2, or 3; or a pharmaceutically-acceptable salt.

20. A compound according to claim 19, or a pharmaceutically-acceptable salt thereof, wherein Y is O and at least one X is a meta-substituent.

21. A compound having the formula,

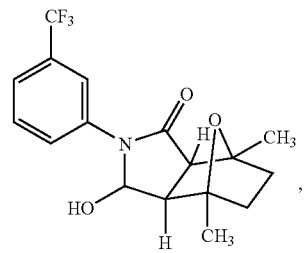

or a pharmaceutically-acceptable salt thereof.

22. The compound according to claim 19, wherein Y is O or a pharmaceutically-acceptable salt thereof.

23. A compound according to claim 22, wherein W is -CR$^7$R$^{7'}$-, or a pharmaceutically-acceptable salt thereof.

24. A compound according to claim 19, having formula,

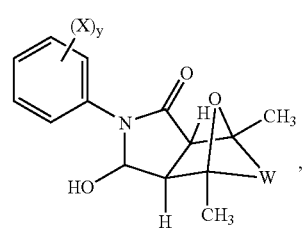

or a pharmaeutically-acceptab;e salt thereof.

25. A compound according to claim 24, wherein W is -CR$^7$R$^{7'}$-CR$^7$R$^{7'}$-, or a pharmaceutically-acceptable salt thereof.

* * * * *

UNITED STATES PATENT AND TRADEMARK OFFICE
CERTIFICATE OF CORRECTION

PATENT NO.       : 7,087,636 B2  
APPLICATION NO.  : 10/322276  
DATED            : August 8, 2006  
INVENTOR(S)      : Salvati et al.

Page 1 of 4

It is certified that error appears in the above-identified patent and that said Letters Patent is hereby corrected as shown below:

Column 61, Lines 38-49,

" 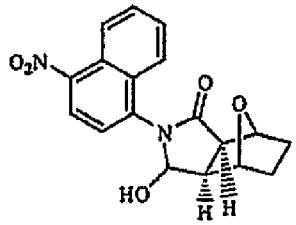 " should read -- 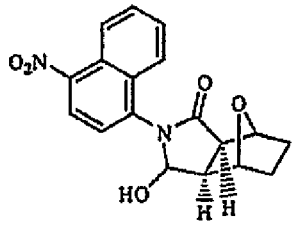 --

Column 62, Lines 7-19,

" 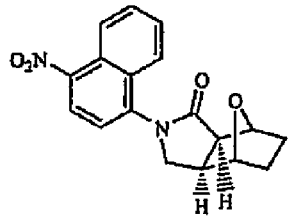 " should read -- 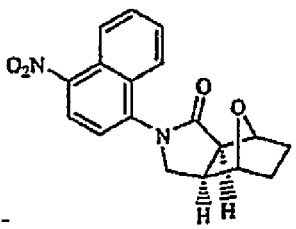 --

Column 66, Lines 57-65,

" 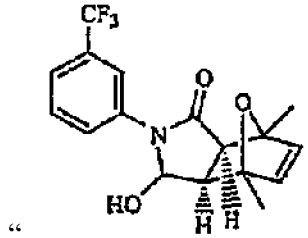 " should read -- 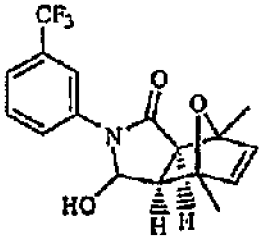 --

Column 67, Lines 8-18,

" 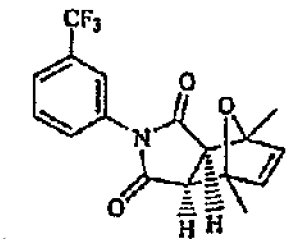 " should read -- 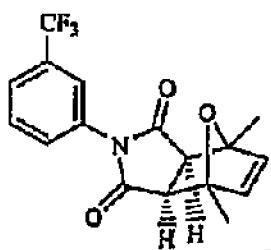 --

UNITED STATES PATENT AND TRADEMARK OFFICE
CERTIFICATE OF CORRECTION

PATENT NO. : 7,087,636 B2
APPLICATION NO. : 10/322276
DATED : August 8, 2006
INVENTOR(S) : Salvati et al.

It is certified that error appears in the above-identified patent and that said Letters Patent is hereby corrected as shown below:

Column 68, Lines 13-23,

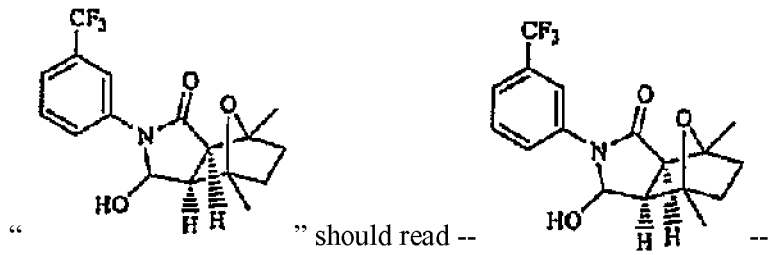

Column 74, Line 57, "substituted aryl, arylalkyl or substituted arylalkyl;" should read --substituted aryl, or arylalkyl or substituted arylalkyl;--

Column 75, Line 11, "$R^7$ and $R^{7'}$" should read --$R^7$, $R^{7'}$, $R^{7a}$, and $R^{7a'}$--

Column 75, Line 42, "$Q_2$ is H or $CH_2OH$" should read --$Q_1$ is H or $CH_2OH$ --

Column 76, Lines 53-54, "(ii) a pharmaceutically acceptable salt." should read --(ii) a pharmaceutically acceptable salt of one of the foregoing compounds in group (i).--

Column 76, Lines 58-64,

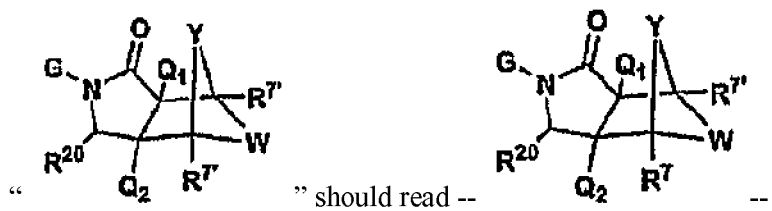

Column 77, Lines 1-9,

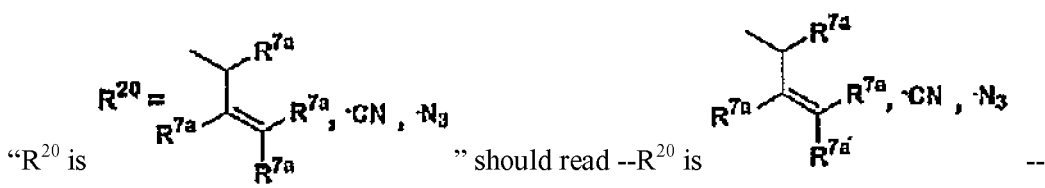

Column 77, Line 11, "in the definition of $R^7$," should read --in the definition of $R^7$ in claim 1 --

UNITED STATES PATENT AND TRADEMARK OFFICE
CERTIFICATE OF CORRECTION

PATENT NO. : 7,087,636 B2
APPLICATION NO. : 10/322276
DATED : August 8, 2006
INVENTOR(S) : Salvati et al.

It is certified that error appears in the above-identified patent and that said Letters Patent is hereby corrected as shown below:

Column 77, Line 35, "said group G substituted with" should read --said group G is substituted with --

Column 77, Lines 61-62, "wherein $R^7$, and $R^{7t}$, $R^{7a}$, and $R^{7a'}$ are" should read --wherein $R^7$, $R^{7'}$, $R^{7a}$, and $R^{7a'}$ are --

Column 77, Line 66, "$SO_2NR^1R^{1t}$," should read --$SO_2NR^1R^{1'}$,--

Column 78, Line 11, "wherein $R^7$, $R^{7'}$, $R^{7a}$, and $R^8$ are" should read --wherein $R^7$, $R^{7a}$, and $R^8$ are --

Column 78, Line 53, "wherein $R^7$, $R^{7'}$, $R^{7a}$, and $R^8$ are" should read --wherein $R^7$, $R^{7a}$, and $R^8$ are --

Column 78, Line 59, "a pharmaceutically-acceptable salt." should read --a pharmaceutically-acceptable salt thereof.--

Column 79, Line 32, "or -$CR^8=CR^{8t}$-; " should read --or -$CR^8=CR^{8'}$-; --

Column 80, Line 14, "or a pharmaceutically-acceptable salt." should read --or a pharmaceutically-acceptable salt thereof. --

Column 80, Lines 34-35, "wherein W is -$CR^7R^{7'}$-, " should read --wherein W is -$CR^7R^{7'}$-$CR^7R^{7'}$-, --

UNITED STATES PATENT AND TRADEMARK OFFICE
CERTIFICATE OF CORRECTION

| | |
|---|---|
| PATENT NO. | : 7,087,636 B2 |
| APPLICATION NO. | : 10/322276 |
| DATED | : August 8, 2006 |
| INVENTOR(S) | : Salvati et al. |

It is certified that error appears in the above-identified patent and that said Letters Patent is hereby corrected as shown below:

<u>Column 80, Lines 49-50,</u> "wherein W is $-CR^7R^{7'}-,$" should read --wherein W is $-CR^7R^{7'}-CR^7R^{7'}-,$ --

Signed and Sealed this

Twenty-fourth Day of April, 2007

JON W. DUDAS
*Director of the United States Patent and Trademark Office*